United States Patent
Garcia-Echeverria et al.

(10) Patent No.: US 7,667,039 B2
(45) Date of Patent: Feb. 23, 2010

(54) 1,3-DIHYDRO-IMIDAZO [4,5-C] QUINOLIN-2-ONES AS LIPID KINASE INHIBITORS

(75) Inventors: Carlos Garcia-Echeverria, Basel (CH); Frédéric Stauffer, Reinach (CH); Pascal Furet, Thann (FR)

(73) Assignee: Novartis AG, Basel (CH)

( * ) Notice: Subject to any disclaimer, the term of this patent is extended or adjusted under 35 U.S.C. 154(b) by 171 days.

(21) Appl. No.: 11/913,788

(22) PCT Filed: May 18, 2006

(86) PCT No.: PCT/EP2006/004725

§ 371 (c)(1),
(2), (4) Date: Nov. 7, 2007

(87) PCT Pub. No.: WO2006/122806

PCT Pub. Date: Nov. 23, 2006

(65) Prior Publication Data

US 2008/0194579 A1    Aug. 14, 2008

(30) Foreign Application Priority Data

May 20, 2005   (GB) .................................. 0510390.8

(51) Int. Cl.
   *C07D 471/04*    (2006.01)
(52) U.S. Cl. .................. 546/82; 544/295; 544/353; 544/361; 514/249; 514/252.18; 514/253.03; 514/293
(58) Field of Classification Search .................. None
See application file for complete search history.

(56) References Cited

FOREIGN PATENT DOCUMENTS

| WO | WO 03/097641 | 11/2003 |
| WO | WO 2005/054237 | 6/2005 |
| WO | WO 2005/054238 | 6/2005 |

OTHER PUBLICATIONS

Vippagunta et al. Advanced Drug Delivery Reviews, vol. 48, pp. 3-26 (2001).*
Maira et al. Expert Opin.Ther.Targets, vol. 12, p. 223-238 (2008).*
Thomas et al. Current Opinion in Pharmacology, vol. 8,p. 267-274 (2008).*
Crabbe et al. Trens in Biochemical Sciences, vol. 32, p. 450-456 (2007).*

* cited by examiner

*Primary Examiner*—Emily Bernhardt
(74) *Attorney, Agent, or Firm*—Oona A. Manzari

(57) ABSTRACT

The invention relates to novel organic compounds of formula (I)

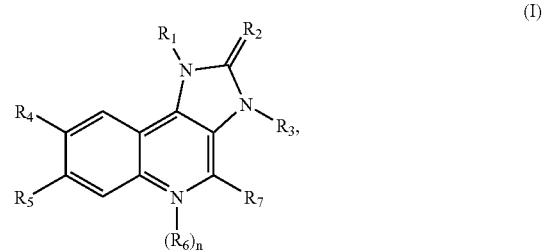

processes for the preparation thereof, the application thereof in a process for the treatment of the human or animal body, the use thereof—alone or in combination with one or more other pharmaceutically active compounds—for the treatment of an inflammatory or obstructive airway disease, such as asthma, disorders commonly occurring in connection with transplantation, or a proliferative disease, such as a tumor disease.

2 Claims, No Drawings

1,3-DIHYDRO-IMIDAZO [4,5-C] QUINOLIN-2-ONES AS LIPID KINASE INHIBITORS

The invention relates to novel organic compounds, processes for the preparation thereof, the application thereof in a process for the treatment of the human or animal body, the use thereof—alone or in combination with one or more other pharmaceutically active compounds—for the treatment of an inflammatory or obstructive airway disease, such as asthma, disorders commonly occurring in connection with transplantation, or a proliferative disease, such as a tumor disease, which may be solid or liquid; a method for the treatment of such a disease in animals, especially in humans, and the use of such a compound—alone or in combination with one or more other pharmaceutically active compounds—for the manufacture of a pharmaceutical preparation for the treatment of said diseases.

The present invention relates to compounds of formula (I)

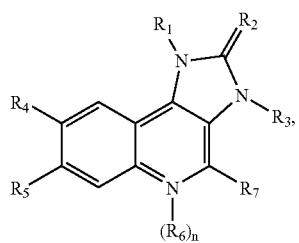

(I)

wherein $R_1$ is naphthyl or phenyl wherein said phenyl is substituted by one or two substituents independently selected from the group consisting of Halogen;

lower alkyl unsubstituted or substituted by halogen, cyano, imidazolyl or triazolyl; cycloalkyl;

amino substituted by one or two substituents independently selected from the group consisting of lower alkyl, lower alkyl sulfonyl, lower alkoxy and lower alkoxy lower alkylamino;

piperazinyl unsubstituted or substituted by one or two substituents independently selected from the group consisting of lower alkyl and lower alkyl sulfonyl;

2-oxo-pyrrolidinyl;

lower alkoxy lower alkyl;

imidazolyl;

pyrazolyl;

and triazolyl;

$R_2$ is O or S;

$R_3$ is lower alkyl;

$R_4$ is pyridyl unsubstituted or substituted by halogen, cyano, lower alkyl, lower alkoxy or piperazinyl unsubstituted or substituted by lower alkyl;

pyrimidinyl unsubstituted or substituted by lower alkoxy;

quinolinyl unsubstituted or substituted by halogen;

quinoxalinyl;

or phenyl substituted with alkoxy $R_5$ is hydrogen or halogen;

n is 0 or 1;

$R_6$ is oxido;

with the proviso that if n=1, the N-atom bearing the radical $R_6$ has a positive charge;

$R_7$ is hydrogen or amino;

or a tautomer thereof, or a pharmaceutically acceptable salt, or a hydrate or solvate thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

In a preferred embodiment, alkyl has up to a maximum of 12 carbon atoms and is especially lower alkyl.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Cycloalkyl is preferably cycloalkyl with from and including 3 up to and including 6 carbon atoms in the ring; cycloalkyl is preferably cyclopropyl, cyclobutyl, cyclopentyl or cyclohexyl.

Alkyl which is substituted by halogen is preferably perfluoro alkyl such as trifluoromethyl.

Halogen is especially fluorine, chlorine, bromine, or iodine, especially fluorine, chlorine, or bromine.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

R1 is preferably phenyl wherein said phenyl is substituted by one or two substituents independently selected from the group consisting of Halogen;

lower alkyl substituted by halogen, cyano, imidazolyl or triazolyl;

amino substituted by one or two substituents independently selected from the group consisting of lower alkyl and lower alkyl sulfonyl;

piperazinyl wherein said piperazinyl is unsubstituted or substituted by one or two lower alkyl substituents;

imidazolyl;

pyrazolyl;

and triazolyl.

R2 is preferably O.

R3 is preferably Me.

R4 is preferably pyrimidinyl or pyridyl unsubstituted or substituted by halogen, cyano, lower alkyl, lower alkoxy or piperazinyl unsubstituted or substituted by lower alkyl;

quinolinyl unsubstituted or substituted by halogen;

quinoxalinyl;

or phenyl substituted with alkoxy.

R5 is preferably hydrogen.

n is preferably 0.

$R_7$ is preferably hydrogen.

A preferred compound is a compound chosen from the group consisting of;

2-Methyl-2-[4-(3-methyl-2-oxo-8-pyridin-4-yl-2,3-dihydro-imidazo[4,5-c]quinolin-1-yl)-phenyl]-propionitrile;

2-Methyl-2-[4-(3-methyl-2-oxo-8-pyridin-3-yl-2,3-dihydro-imidazo[4,5-c]quinolin-1-yl)-phenyl]-propionitrile;

2-{4-[8-(6-Methoxy-pyridin-3-yl)-3-methyl-2-oxo-2,3-dihydro-imidazo[4,5-c]quinolin-1-yl]-phenyl}-2-methyl-propionitrile;

2-{4-[8-(5-Methoxy-pyridin-3-yl)-3-methyl-2-oxo-2,3-dihydro-imidazo[4,5-c]quinolin-2-yl]-phenyl}-2-methyl-propionitrile;

2-Methyl-2-{4-[3-methyl-2-oxo-8-(6-piperazin-1-yl-pyridin-3-yl)-2,3-dihydro-imidazo[4,5-c]quinolin-1-yl]-phenyl}-propionitrile;

2-Methyl-2-(4-{3-methyl-8-[2-(4-methyl-piperazin-1-yl)-pyridin-4-yl]-2-oxo-2,3-dihydro-imidazo[4,5-c]quinolin-1-yl}-phenyl)-propionitrile;

2-Methyl-2-[4-(3-methyl-2-oxo-8-quinolin-3-yl-2,3-dihydro-imidazo[4,5-c]quinolin-1-yl)-phenyl]-propionitrile;

2-{4-[8-(2-Fluoro-quinolin-3-yl)-3-methyl-2-oxo-2,3-dihydro-imidazo[4,5-c]quinolin-1-yl]-phenyl}-2-methyl-propionitrile;

2-Methyl-2-[4-(3-methyl-2-oxo-8-quinolin-6-yl-2,3-dihydro-imidazo[4,5-c]quinolin-1-yl)-phenyl]-propionitrile;

2-Methyl-2-[4-(3-methyl-2-oxo-8-quinolin-5-yl-2,3-dihydro-imidazo[4,5-c]quinolin-1-yl)-phenyl]-propionitrile;

2-Methyl-2-[4-(3-methyl-2-oxo-8-quinoxalin-6-yl-2,3-dihydro-imidazo[4,5-c]quinolin-1-yl)-phenyl]-propionitrile;

2-Ethyl-2-[4-(3-methyl-2-oxo-8-pyridin-3-yl-2,3-dihydro-imidazo[4,5-c]quinolin-1-yl)-phenyl]-butyronitrile;

2-Ethyl-2-[4-(3-methyl-2-oxo-8-quinolin-3-yl-2,3-dihydro-imidazo[4,5-c]quinolin-1-yl)-phenyl]-butyronitrile;

1-[3-Fluoro-4-(2-oxo-pyrrolidin-1-yl)-phenyl]-3-methyl-8-pyridin-3-yl-1,3-dihydro-imidazo[4,5-c]quinolin-2-one;

1-[3-Fluoro-4-(2-oxo-pyrrolidin-1-yl)-phenyl]-3-methyl-8-quinolin-3-yl-1,3-dihydro-imidazo[4,5-c]quinolin-2-one;

3-Methyl-1-[4-(2-oxo-pyrrolidin-1-yl)-phenyl]-8-pyridin-3-yl-1,3-dihydro-imidazo[4,5-c]quinolin-2-one;

3-Methyl-1-[4-(2-oxo-pyrrolidin-1-yl)-phenyl]-8-quinolin-3-yl-1,3-dihydro-imidazo[4,5-c]quinolin-2-one;

1-{4-[Bis-(2-methoxy-ethyl)-amino]-3-fluoro-phenyl}-3-methyl-8-pyridin-3-yl-1,3-dihydro-imidazo[4,5-c]quinolin-2-one;

1-{4-[Bis-(2-methoxy-ethyl)-amino]-3-fluoro-phenyl}-3-methyl-8-quinolin-3-yl-1,3-dihydro-imidazo[4,5-c]quinolin-2-one;

1-{4-[Bis-(2-methoxy-ethyl)-amino]-phenyl}-3-methyl-8-pyridin-3-yl-1,3-dihydro-imidazo[4,5-c]quinolin-2-one;

1-{4-[Bis-(2-methoxy-ethyl)-amino]-phenyl}-3-methyl-8-quinolin-3-yl-1,3-dihydro-imidazo[4,5-c]quinolin-2-one;

3-Methyl-1-naphthalen-2-yl-8-pyridin-3-yl-1,3-dihydro-imidazo[4,5-c]quinolin-2-one;

3-Methyl-1-naphthalen-2-yl-8-quinolin-3-yl-1,3-dihydro-imidazo[4,5-c]quinolin-2-one;

1-(2-Chloro-phenyl)-3-methyl-8-pyridin-3-yl-1,3-dihydro-imidazo[4,5-c]quinolin-2-one;

1-(2-Chloro-phenyl)-3-methyl-8-quinolin-3-yl-1,3-dihydro-imidazo[4,5-c]quinolin-2-one;

3-Methyl-8-pyridin-3-yl-1-o-tolyl-1,3-dihydro-imidazo[4,5-c]quinolin-2-one;

3-Methyl-8-quinolin-3-yl-1-o-tolyl-1,3-dihydro-imidazo[4,5-c]quinolin-2-one;

1-(2-Ethyl-phenyl)-3-methyl-8-pyridin-3-yl-1,3-dihydro-imidazo[4,5-c]quinolin-2-one;

1-(2-Ethyl-phenyl)-3-methyl-8-quinolin-3-yl-1,3-dihydro-imidazo[4,5-c]quinolin-2-one;

3-Methyl-8-pyridin-3-yl-1-(2-trifluoromethyl-phenyl)-1,3-dihydro-imidazo[4,5-c]quinolin-2-one;

3-Methyl-8-quinolin-3-yl-1-(2-trifluoromethyl-phenyl)-1,3-dihydro-imidazo[4,5-c]quinolin-2-one;

1-(4-Fluoro-2-methyl-phenyl)-3-methyl-8-quinolin-3-yl-1,3-dihydro-imidazo[4,5-c]quinolin-2-one;

1-(4-Fluoro-2-methyl-phenyl)-3-methyl-8-quinolin-3-yl-1,3-dihydro-imidazo[4,5-c]quinolin-2-one;

1-(2-Chloro-4-fluoro-phenyl)-3-methyl-8-pyridin-3-yl-1,3-dihydro-imidazo[4,5-c]quinolin-2-one;

1-(2-Chloro-4-fluoro-phenyl)-3-methyl-8-quinolin-3-yl-1,3-dihydro-imidazo[4,5-c]quinolin-2-one;

1-(3-Chloro-phenyl)-3-methyl-8-pyridin-3-yl-1,3-dihydro-imidazo[4,5-c]quinolin-2-one;

1-(3-Chloro-phenyl)-3-methyl-8-quinolin-3-yl-1,3-dihydro-imidazo[4,5-c]quinolin-2-one;

3-Methyl-8-pyridin-3-yl-1-(3-trifluoromethyl-phenyl)-1,3-dihydro-imidazo[4,5-c]quinolin-2-one;

3-Methyl-8-quinolin-3-yl-1-(3-trifluoromethyl-phenyl)-1,3-dihydro-imidazo[4,5-c]quinolin-2-one;

1-(4-Methoxymethyl-phenyl)-3-methyl-8-pyridin-3-yl-1,3-dihydro-imidazo[4,5-c]quinolin-2-one;

1-(4-Methoxymethyl-phenyl)-3-methyl-8-quinolin-3-yl-1,3-dihydro-imidazo[4,5-c]quinolin-2-one;

1-[2-Chloro-4-(2-methoxy-ethyl)-phenyl]-3-methyl-8-pyridin-3-yl-1,3-dihydro-imidazo[4,5-c]quinolin-2-one;

1-[2-Chloro-4-(2-methoxy-ethyl)-phenyl]-3-methyl-8-quinolin-3-yl-1,3-dihydro-imidazo[4,5-c]quinolin-2-one;
1-[4-(2-Methoxy-ethyl)-phenyl]-3-methyl-8-quinolin-3-yl-1,3-dihydro-imidazo[4,5-c]quinolin-2-one;
1-[4-(2-Methoxy-ethyl)-phenyl]-3-methyl-8-pyridin-3-yl-1,3-dihydro-imidazo[4,5-c]quinolin-2-one;
2-Methyl-2-[4-(3-methyl-2-oxo-5-oxy-8-pyridin-3-yl-2,3-dihydro-imidazo[4,5-c]quinolin-2-yl)-phenyl]-propionitrile;
2-Methyl-2-[4-(3-methyl-2-oxo-5-oxy-8-quinolin-3-yl-2,3-dihydro-imidazo[4,5-c]quinolin-1-yl)-phenyl]-propionitrile;
2-[4-(7-Fluoro-3-methyl-2-oxo-8-pyridin-3-yl-2,3-dihydro-imidazo[4,5-c]quinolin-1-yl)-phenyl]-2-methyl-propionitrile;
2-[4-(7-Fluoro-3-methyl-2-oxo-8-quinolin-3-yl-2,3-dihydro-imidazo[4,5-c]quinolin-1-yl)-phenyl]-2-methyl-propionitrile;
N-Methyl-N-[4-(3-methyl-2-oxo-8-pyridin-3-yl-2,3-dihydro-imidazo[4,5-c]quinolin-1-yl)-phenyl]-methanesulfonamide;
Methyl-[4-(3-methyl-2-oxo-8-pyridin-3-yl-2,3-dihydro-imidazo[4,5-c]quinolin-1-yl)-phenyl]-carbamic acid tert-butyl ester;
Ethanesulfonic acid methyl-[4-(3-methyl-2-oxo-8-pyridin-3-yl-2,3-dihydro-imidazo[4,5-c]quinolin-1-yl)-phenyl]-amide;
Ethanesulfonic acid methyl-[4-(3-methyl-2-oxo-8-quinolin-3-yl-2,3-dihydro-imidazo[4,5-c]quinolin-1-yl)-phenyl]-amide;
N-Ethyl-N-[4-(3-methyl-2-oxo-8-pyridin-3-yl-2,3-dihydro-imidazo[4,5-c]quinolin-1-yl)-phenyl]-methanesulfonamide;
N-Ethyl-N-[4-(3-methyl-2-oxo-8-quinolin-3-yl-2,3-dihydro-imidazo[4,5-c]quinolin-1-yl)-phenyl]-methanesulfonamide;
2-[4-(3-Ethyl-2-oxo-8-pyridin-3-yl-2,3-dihydro-imidazo[4,5-c]quinolin-1-yl)-phenyl]-2-methyl-propionitrile;
1-[3-Fluoro-4-(4-methanesulfonyl-piperazin-1-yl)-phenyl]-3-methyl-8-quinolin-3-yl-1,3-dihydro-imidazo[4,5-c]quinolin-2-one;
1-[3-Fluoro-4-(4-methanesulfonyl-piperazin-1-yl)-phenyl]-3-methyl-8-pyridin-3-yl-1,3-dihydro-imidazo[4,5-c]quinolin-2-one;
1-(3-Fluoro-4-piperazin-1-yl-phenyl)-3-methyl-8-quinolin-3-yl-1,3-dihydro-imidazo[4,5-c]quinolin-2-one;
1-(3-Fluoro-4-piperazin-1-yl-phenyl)-3-methyl-8-pyridin-3-yl-1,3-dihydro-imidazo[4,5-c]quinolin-2-one;
3-Methyl-1-[4-(4-methyl-piperazin-1-yl)-phenyl]-8-quinolin-3-yl-1,3-dihydro-imidazo[4,5-c]quinolin-2-one;
3-Methyl-1-[4-(4-methyl-piperazin-1-yl)-phenyl]-8-pyridin-3-yl-1,3-dihydro-imidazo[4,5-c]quinolin-2-one;
1-[2-Chloro-4-(4-methyl-piperazin-1-yl)-phenyl]-3-methyl-8-quinolin-3-yl-1,3-dihydro-imidazo[4,5-c]quinolin-2-one;
1-[2-Chloro-4-(4-methyl-piperazin-1-yl)-phenyl]-3-methyl-8-pyridin-3-yl-1,3-dihydro-imidazo[4,5-c]quinolin-2-one;
1-[3-Chloro-4-(4-methyl-piperazin-1-yl)-phenyl]-3-methyl-8-quinolin-3-yl-1,3-dihydro-imidazo[4,5-c]quinolin-2-one;
1-[3-Chloro-4-(4-methyl-piperazin-1-yl)-phenyl]-3-methyl-8-pyridin-3-yl-1,3-dihydro-imidazo[4,5-c]quinolin-2-one;
1-(4-Imidazol-1-yl-2-methyl-phenyl)-3-methyl-8-quinolin-3-yl-1,3-dihydro-imidazo[4,5-c]quinolin-2-one;
1-(4-Imidazol-1-yl-2-methyl-phenyl)-3-methyl-8-pyridin-3-yl-1,3-dihydro-imidazo[4,5-c]quinolin-2-one;
3-Methyl-1-(4-pyrazol-1-yl-phenyl)-8-quinolin-3-yl-1,3-dihydro-imidazo[4,5-c]quinolin-2-one;
3-Methyl-1-(4-pyrazol-1-yl-phenyl)-8-pyridin-3-yl-1,3-dihydro-imidazo[4,5-c]quinolin-2-one;
3-Methyl-8-quinolin-3-yl-1-(4-[1,2,4]triazol-1-yl-phenyl)-1,3-dihydro-imidazo[4,5-c]quinolin-2-one;
3-Methyl-8-pyridin-3-yl-1-(4-[1,2,4]triazol-1-yl-phenyl)-1,3-dihydro-imidazo[4,5-c]quinolin-2-one;
3-Methyl-1-[4-(4-methyl-piperazin-1-yl)-3-trifluoromethyl-phenyl]-8-quinolin-3-yl-1,3-dihydro-imidazo[4,5-c]quinolin-2-one;
3-Methyl-1-[4-(4-methyl-piperazin-1-yl)-3-trifluoromethyl-phenyl]-8-pyridin-3-yl-1,3-dihydro-imidazo[4,5-c]quinolin-2-one;
1-(3-Chloro-4-piperazin-1-yl-phenyl)-3-methyl-8-quinolin-3-yl-1,3-dihydro-imidazo[4,5-c]quinolin-2-one;
1-(3-Chloro-4-piperazin-1-yl-phenyl)-3-methyl-8-pyridin-3-yl-1,3-dihydro-imidazo[4,5-c]quinolin-2-one;
1-(3-Chloro-4-piperazin-1-yl-phenyl)-8-(6-methoxy-pyridin-3-yl)-3-methyl-1,3-dihydro-imidazo[4,5-c]quinolin-2-one;
1-(3-Chloro-4-piperazin-1-yl-phenyl)-8-(5-methoxy-pyridin-3-yl)-3-methyl-1,3-dihydro-imidazo[4,5-c]quinolin-2-one;
8-(6-Methoxy-pyridin-3-yl)-3-methyl-1-[4-(4-methyl-piperazin-1-yl)-3-trifluoromethyl-phenyl]-1,3-dihydro-imidazo[4,5-c]quinolin-2-one;
8-(5-Methoxy-pyridin-3-yl)-3-methyl-1-[4-(4-methyl-piperazin-1-yl)-3-trifluoromethyl-phenyl]-1,3-dihydro-imidazo[4,5-c]quinolin-2-one;
1-[2-Chloro-4-(4-methyl-piperazin-1-yl)-phenyl]-8-(6-methoxy-pyridin-3-yl)-3-methyl-1,3-dihydro-imidazo[4,5-c]quinolin-2-one;
1-[2-Chloro-4-(4-methyl-piperazin-1-yl)-phenyl]-8-(5-methoxy-pyridin-3-yl)-3-methyl-1,3-dihydro-imidazo[4,5-c]quinolin-2-one;
1-(3-Chloro-4-piperazin-1-yl-phenyl)-3-methyl-8-quinoxalin-6-yl-1,3-dihydro-imidazo[4,5-c]quinolin-2-one;
3-Methyl-1-(4-piperazin-1-yl-3-trifluoromethyl-phenyl)-8-quinolin-3-yl-1,3-dihydro-imidazo[4,5-c]quinolin-2-one;
3-Methyl-1-(4-piperazin-1-yl-3-trifluoromethyl-phenyl)-8-pyridin-3-yl-1,3-dihydro-imidazo[4,5-c]quinolin-2-one;
8-(6-Methoxy-pyridin-3-yl)-3-methyl-1-(4-piperazin-1-yl-3-trifluoromethyl-phenyl)-1,3-dihydro-imidazo[4,5-c]quinolin-2-one;
8-(5-Methoxy-pyridin-3-yl)-3-methyl-1-(4-piperazin-1-yl-3-trifluoromethyl-phenyl)-1,3-dihydro-imidazo[4,5-c]quinolin-2-one;
3-Methyl-1-(4-piperazin-1-yl-3-trifluoromethyl-phenyl)-8-quinoxalin-6-yl-1,3-dihydro-imidazo[4,5-c]quinolin-2-one;
1-[3-Chloro-4-(cis-3,5-dimethyl-piperazin-1-yl)-phenyl]-3-methyl-8-pyridin-3-yl-1,3-dihydro-imidazo[4,5-c]quinolin-2-one;
1-[3-Chloro-4-(cis-3,5-dimethyl-piperazin-1-yl)-phenyl]-3-methyl-8-quinolin-3-yl-1,3-dihydro-imidazo[4,5-c]quinolin-2-one;
1-[3-Chloro-4-(4-ethyl-piperazin-1-yl)-phenyl]-3-methyl-8-pyridin-3-yl-1,3-dihydro-imidazo[4,5-c]quinolin-2-one;
1-[3-Chloro-4-(4-ethyl-piperazin-1-yl)-phenyl]-3-methyl-8-quinolin-3-yl-1,3-dihydro-imidazo[4,5-c]quinolin-2-one;
1-[3-Chloro-4-(4-isopropyl-piperazin-1-yl)-phenyl]-3-methyl-8-pyridin-3-yl-1,3-dihydro-imidazo[4,5-c]quinolin-2-one;

1-[3-Chloro-4-(4-isopropyl-piperazin-1-yl)-phenyl]-3-methyl-8-quinolin-3-yl-1,3-dihydro-imidazo[4,5-c]quinolin-2-one;
1-[3-Chloro-4-(4-isopropyl-piperazin-1-yl)-phenyl]-3-methyl-8-quinolin-3-yl-1,3-dihydro-imidazo[4,5-c]quinolin-2-one;
1-[3-Chloro-4-(4-isopropyl-piperazin-1-yl)-phenyl]-3-methyl-8-quinolin-3-yl-1,3-dihydro-imidazo[4,5-c]quinolin-2-one;
1-[4-(4-Ethyl-piperazin-1-yl)-3-trifluoromethyl-phenyl]-3-methyl-8-pyridin-3-yl-1,3-dihydro-imidazo[4,5-c]quinolin-2-one;
1-[4-(4-Ethyl-piperazin-1-yl)-3-trifluoromethyl-phenyl]-3-methyl-8-quinolin-3-yl-1,3-dihydro-imidazo[4,5-c]quinolin-2-one;
1-[4-(4-Ethyl-piperazin-1-yl)-3-trifluoromethyl-phenyl]-3-methyl-8-pyridin-3-yl-1,3-dihydro-imidazo[4,5-c]quinolin-2-one;
1-[4-(4-Ethyl-piperazin-1-yl)-3-trifluoromethyl-phenyl]-3-methyl-8-quinolin-3-yl-1,3-dihydro-imidazo[4,5-c]quinolin-2-one;
3-Methyl-8-(6-piperazin-1-yl-pyridin-3-yl)-1-(3-trifluoromethyl-phenyl)-1,3-dihydro-imidazo[4,5-c]quinolin-2-one;
8-(6-Methoxy-pyridin-3-yl)-3-methyl-1-(3-trifluoromethyl-phenyl)-1,3-dihydro-imidazo[4,5-c]quinolin-2-one;
8-(6-Methoxy-pyridin-3-yl)-3-methyl-1-(3-trifluoromethyl-phenyl)-1,3-dihydro-imidazo[4,5-c]quinolin-2-one;
1-(3-Chloro-4-imidazol-1-yl-phenyl)-3-methyl-8-pyridin-3-yl-1,3-dihydro-imidazo[4,5-c]quinolin-2-one;
1-(3-Chloro-4-imidazol-1-yl-phenyl)-3-methyl-8-quinolin-3-yl-1,3-dihydro-imidazo[4,5-c]quinolin-2-one;
2-Methyl-2-[4-(3-methyl-8-quinolin-3-yl-2-thioxo-2,3-dihydro-imidazo[4,5-c]quinolin-1-yl)-phenyl]-propionitrile;
2-Methyl-2-{4-[3-methyl-8-(2-methyl-pyridin-4-yl)-2-oxo-2,3-dihydro-imidazo[4,5-c]quinolin-1-yl)-yl]-phenyl}-propionitrile;
5-{1-[4-(Cyano-dimethyl-methyl)-phenyl]-3-methyl-2-oxo-2,3-dihydro-1H-imidazo[4,5-c]quinolin-8-yl}-pyridine-2-carbonitrile;
2-[4-(4-Amino-3-methyl-2-oxo-8-quinolin-3-yl-2,3-dihydro-imidazo[4,5-c]quinolin-1-yl)-phenyl]-2-methyl-propionitrile;
1-[4-(3-Methyl-2-oxo-8-pyridin-3-yl-2,3-dihydro-imidazo[4,5-c]quinolin-1-yl)-phenyl]-cyclopropanecarbonitrile;
1-[4-(3-Methyl-2-oxo-8-quinolin-3-yl-2,3-dihydro-imidazo[4,5-c]quinolin-1-yl)-phenyl]-cyclopropanecarbonitrile;
1-{4-[8-(6-Methoxy-pyridin-3-yl)-3-methyl-2-oxo-2,3-dihydro-imidazo[4,5-c]quinolin-1-yl]-phenyl}-cyclopropanecarbonitrile;
1-[3-Chloro-4-(4-methyl-piperazin-1-yl)-phenyl]-8-(6-methoxy-pyridin-3-yl)-3-methyl-1,3-dihydro-imidazo[4,5-c]quinolin-2-one;
1-[3-Chloro-4-(4-methyl-piperazin-1-yl)-phenyl]-8-(5-methoxy-pyridin-3-yl)-3-methyl-1,3-dihydro-imidazo[4,5-c]quinolin-2-one;
1-[3-Chloro-4-(4-methyl-piperazin-1-yl)-phenyl]-3-methyl-8-quinoxalin-6-yl-1,3-dihydro-imidazo[4,5-c]quinolin-2-one;
1-(3-Chloro-4-piperazin-1-yl-phenyl)-8-(2-methoxy-pyrimidin-5-yl)-3-methyl-1,3-dihydro-imidazo[4,5-c]quinolin-2-one;
1-(3-Chloro-4-piperazin-1-yl-phenyl)-3-methyl-8-pyrimidin-5-yl-1,3-dihydro-imidazo[4,5-c]quinolin-2-one;
1-(3-Chloro-4-piperazin-1-yl-phenyl)-8-(2-methoxy-pyrimidin-5-yl)-3-methyl-1,3-dihydro-imidazo[4,5-c]quinolin-2-one;
1-(3-Chloro-4-piperazin-1-yl-phenyl)-3-methyl-8-pyrimidin-5-yl-1,3-dihydro-imidazo[4,5-c]quinolin-2-one;
1-(3-Chloro-4-piperazin-1-yl-phenyl)-3-methyl-8-(2-methyl-pyridin-4-yl)-1,3-dihydro-imidazo[4,5-c]quinolin-2-one;
1-[3-Chloro-4-(cis-3,5-dimethyl-piperazin-1-yl)-phenyl]-8-(6-methoxy-pyridin-3-yl)-3-methyl-1,3-dihydro-imidazo[4,5-c]quinolin-2-one;
1-[4-(cis-3,5-Dimethyl-piperazin-1-yl)-phenyl]-8-(5-methoxy-pyridin-3-yl)-3-methyl-1,3-dihydro-imidazo[4,5-c]quinolin-2-one;
1-[4-(cis-3,5-Dimethyl-piperazin-1-yl)-3-trifluoromethyl-phenyl]-8-(6-methoxy-pyridin-3-yl)-3-methyl-1,3-dihydro-imidazo[4,5-c]quinolin-2-one;
1-[4-(cis-3,5-Dimethyl-piperazin-1-yl)-3-trifluoromethyl-phenyl]-8-(5-methoxy-pyridin-3-yl)-3-methyl-1,3-dihydro-imidazo[4,5-c]quinolin-2-one;
8-(2-Methoxy-pyrimidin-5-yl)-3-methyl-1-(4-piperazin-1-yl-3-trifluoromethyl-phenyl)-1,3-dihydro-imidazo[4,5-c]quinolin-2-one;
3-Methyl-1-(4-piperazin-1-yl-3-trifluoromethyl-phenyl)-8-pyrimidin-5-yl-1,3-dihydro-imidazo[4,5-c]quinolin-2-one;
5-[3-Methyl-2-oxo-1-(4-piperazin-1-yl-3-trifluoromethyl-phenyl)-2,3-dihydro-1H-imidazo[4,5-c]quinolin-8-yl]-pyridine-2-carbonitrile;
3-Methyl-8-(2-methyl-pyridin-4-yl)-1-(4-piperazin-1-yl-3-trifluoromethyl-phenyl)-1,3-dihydro-imidazo[4,5-c]quinolin-2-one;
8-(3,4-Dimethoxy-phenyl)-3-methyl-1-(4-piperazin-1-yl-3-trifluoromethyl-phenyl)-1,3-dihydro-imidazo[4,5-c]quinolin-2-one;
3-Methyl-8-pyridin-3-yl-1-(4-[1,2,4]triazol-1-yl-3-trifluoromethyl-phenyl)-1,3-dihydro-imidazo[4,5-c]quinolin-2-one;
3-Methyl-8-quinolin-3-yl-1-(4-[1,2,4]triazol-1-yl-3-trifluoromethyl-phenyl)-1,3-dihydro-imidazo[4,5-c]quinolin-2-one;
8-(6-Methoxy-pyridin-3-yl)-3-methyl-1-(4-[1,2,4]triazol-1-yl-3-trifluoromethyl-phenyl)-1,3-dihydro-imidazo[4,5-c]quinolin-2-one;
8-(5-Methoxy-pyridin-3-yl)-3-methyl-1-(4-[1,2,4]triazol-1-yl-3-trifluoromethyl-phenyl)-1,3-dihydro-imidazo[4,5-c]quinolin-2-one;
5-[3-Methyl-2-oxo-1-(4-[1,2,4]triazol-1-yl-3-trifluoromethyl-phenyl)-2,3-dihydro-1H-imidazo[4,5-c]quinolin-8-yl]-pyridine-2-carbonitrile;
8-(6-Fluoro-pyridin-3-yl)-3-methyl-1-(4-[1,2,4]triazol-1-yl-3-trifluoromethyl-phenyl)-1,3-dihydro-imidazo[4,5-c]quinolin-2-one;
8-(2,6-Dimethoxy-pyridin-3-yl)-3-methyl-1-(4-[1,2,4]triazol-1-yl-3-trifluoromethyl-phenyl)-1,3-dihydro-imidazo[4,5-c]quinolin-2-one;
3-Methyl-8-pyrimidin-5-yl-1-(4-[1,2,4]triazol-1-yl-3-trifluoromethyl-phenyl)-1,3-dihydro-imidazo[4,5-c]quinolin-2-one;
8-(2-Methoxy-pyrimidin-5-yl)-3-methyl-1-(4-[1,2,4]triazol-1-yl-3-trifluoromethyl-phenyl)-1,3-dihydro-imidazo[4,5-c]quinolin-2-one;
8-(2,4-Dimethoxy-pyrimidin-5-yl)-3-methyl-1-(4-[1,2,4]triazol-1-yl-3-trifluoromethyl-phenyl)-1,3-dihydro-imidazo[4,5-c]quinolin-2-one;
3-Methyl-1-(4-pyrazol-1-yl-3-trifluoromethyl-phenyl)-8-pyridin-3-yl-1,3-dihydro-imidazo[4,5-c]quinolin-2-one;
3-Methyl-1-(4-pyrazol-1-yl-3-trifluoromethyl-phenyl)-8-quinolin-3-yl-1,3-dihydro-imidazo[4,5-c]quinolin-2-one;

8-(6-Methoxy-pyridin-3-yl)-3-methyl-1-(4-pyrazol-1-yl-3-trifluoromethyl-phenyl)-1,3-dihydro-imidazo[4,5-c]quinolin-2-one;
8-(5-Methoxy-pyridin-3-yl)-3-methyl-1-(4-pyrazol-1-yl-3-trifluoromethyl-phenyl)-1,3-dihydro-imidazo[4,5-c]quinolin-2-one;
1-(3-Chloro-4-[1,2,4]triazol-1-yl-phenyl)-3-methyl-8-pyridin-3-yl-1,3-dihydro-imidazo[4,5-c]quinolin-2-one;
1-(3-Chloro-4-[1,2,4]triazol-1-yl-phenyl)-3-methyl-8-quinolin-3-yl-1,3-dihydro-imidazo[4,5-c]quinolin-2-one;
1-(4-Imidazol-1-yl-3-trifluoromethyl-phenyl)-3-methyl-8-pyridin-3-yl-1,3-dihydro-imidazo[4,5-c]quinolin-2-one;
1-(4-Imidazol-1-yl-3-trifluoromethyl-phenyl)-3-methyl-8-quinolin-3-yl-1,3-dihydro-imidazo[4,5-c]quinolin-2-one;
1-(4-Imidazol-1-yl-3-trifluoromethyl-phenyl)-8-(6-methoxy-pyridin-3-yl)-3-methyl-1,3-dihydro-imidazo[4,5-c]quinolin-2-one;
1-(4-Imidazol-1-yl-3-trifluoromethyl-phenyl)-8-(5-methoxy-pyridin-3-yl)-3-methyl-1,3-dihydro-imidazo[4,5-c]quinolin-2-one;
3-Methyl-8-pyridin-3-yl-1-(4-[1,2,4]triazol-1-ylmethyl-phenyl)-1,3-dihydro-imidazo[4,5-c]quinolin-2-one;
3-Methyl-8-quinolin-3-yl-1-(4-[1,2,4]triazol-1-ylmethyl-phenyl)-1,3-dihydro-imidazo[4,5-c]quinolin-2-one;
1-(4-Imidazol-1-ylmethyl-phenyl)-3-methyl-8-pyridin-3-yl-1,3-dihydro-imidazo[4,5-c]quinolin-2-one; and
1-(4-Imidazol-1-ylmethyl-phenyl)-3-methyl-8-quinolin-3-yl-1,3-dihydro-imidazo[4,5-c]quinolin-2-one;

or a tautomer thereof, or a pharmaceutically acceptable salt, or a hydrate or solvate thereof.

Preferred are also compounds of formula Ia,

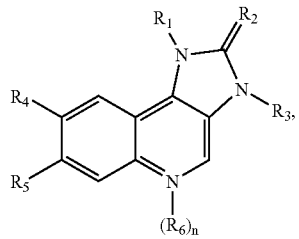

(Ia)

wherein $R_1$ is naphthyl or phenyl wherein said phenyl is substituted by one or two substituents independently selected from the group consisting of Halogen;

lower alkyl unsubstituted or substituted by halo or cyano;

amino substituted by one or two substituents independently selected from the group consisting of lower alkyl, lower alkyl sulfonyl, lower alkoxy and lower alkoxy lower alkylamino;

piperazinyl wherein said piperazinyl is unsubstituted or substituted by one or two substituents independently selected from the group consisting of lower alkyl and lower alkyl sulfonyl;

2-oxo-pyrrolidinyl;

lower alkoxy lower alkyl;

imidazolyl;

pyrazolyl and triazolyl;

$R_2$ is O or S;

$R_3$ is lower alkyl;

$R_4$ is pyridyl unsubstituted or substituted by lower alkoxy or piperazinyl unsubstituted or substituted by lower alkyl, or quinolinyl unsubstituted or substituted by halogen, or quinoxalinyl;

$R_5$ is hydrogen or halogen;

n is 0 or 1;

$R_6$ is oxido;

with the proviso that if n=1, the N-atom bearing the radical $R_6$ has a positive charge;

or a tautomer thereof, or a pharmaceutically acceptable salt, or a hydrate or solvate thereof.

Surprisingly, it has now been found that the compounds of formula I, have advantageous pharmacological properties and inhibit the activity of the lipid kinases, such as the PI3-kinase and/or members of the PI3-kinase-related protein kinase family (also called PIKK and include DNA-PK, ATM, ATR, hSMG-1 and mTOR), such as the DNA protein-kinase, and may be used to treat disease or disorders which depend on the activity of said kinases.

Having regard to their inhibition of phosphatidylinositol 3-kinase enzymes, compounds of formula (I) in free or pharmaceutically acceptable salt form, are useful in the treatment of conditions which are mediated by the activation of the PI3 kinase enzymes, such as proliferative, inflammatory or allergic conditions, or disorders commonly occurring in connection with transplantation.

Treatment in accordance with the invention may be symptomatic or prophylactic.

Preferred is a compound of formula (I) for use in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

Compounds according to the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds according to formula I can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Compounds of the invention may also be used for the treatment of other diseases or conditions, such as diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Furthermore, the invention provides the use of a compound according to the definitions herein, or a pharmaceutically acceptable salt, or a hydrate or solvate thereof for the preparation of a medicament for the treatment of a proliferative disease, an inflammatory disease or an obstructive respiratory disease, or a disorder commonly occurring in connection with transplantation.

The efficacy of the compounds of formula I and salts thereof as PI3 kinase inhibitors can be demonstrated as follows:

The kinase reaction was performed in a final volume of 50 µL per well of a half area COSTAR, 96 well plate. The final concentrations of ATP and phosphatidyl inositol in the assay were 5 µM and 6 µg/mL respectively. The reaction was started by the addition of PI3 kinase p110β. The components of the assay were added per well as follows:

10 µL test compound in 5% DMSO per well in columns 2-1.

Total activity was determined by addition 10 µL of 5% vol/vol DMSO in the first 4 wells of column 1 and the last 4 wells of column 12.

The background was determined by addition of 10 µM control compound to the last 4 wells of column 1 and the first 4 wells of column 12.

2 mL 'Assay mix' were prepared per plate:
   1.912 mL of HEPES assay buffer
   8.33 µL of 3 mM stock of ATP giving a final concentration of 5 µM per well
   1 µL of [$^{33}$P]ATP on the activity date giving 0.05 µCi per well
   30 µL of 1 mg/mL PI stock giving a final concentration of 6 µg/mL per well
   5 µL of 1 M stock $MgCl_2$ giving a final concentration of 1 mM per well 20 µL of the assay mix were added/well.

2 mL 'Enzyme mix' were prepared per plate (x µL PI3 kinase p110β in 2 mL of kinase buffer). The 'Enzyme mix' was kept on ice during addition to the assay plates.

20 µl 'Enzyme mix' were added/well to start the reaction.

The plate was then incubated at room temperature for 90 minutes.

The reaction was terminated by the addition of 50 µL WGA-SPA bead suspension per well.

The assay plate was sealed using TopSeal-S and incubated at room temperature for at least 60 minutes.

The assay plate was then centrifuged at 1500 rpm for 2 minutes using the Jouan bench top centrifuge.

The assay plate was counted using a Packard TopCount, each well being counted for 20 seconds.
   The volume of enzyme will be dependent on the enzymatic activity of the batch in use.

Some of the compounds show a certain level of selectivity against the different paralogs PI3K alpha, gamma and delta.

Description of Biochemical Assay for DNA-PK:

The assay was done using the kit V7870 from Promega, that quantitated DNA-dependent protein kinase activity, both in purified enzyme preparations and in cell nuclear extracts. DNA-PK is a nuclear serine/threonine protein kinase that requires double-stranded DNA (dsDNA) for activity. The binding of dsDNA to the enzyme results in the formation of the active enzyme and also brings the substrate closer to the enzyme, allowing the phosphorylation reaction to proceed.

DNA-PK X5 reaction buffer (250 mM HEPES, 500 mM KCl, 50 mM $MgCl_2$, 1 mM EGTA, 0.5 mM EDTA, 5 mM DTT, pH to 7.5 with KOH) was diluted 1/5 in deionised water and BSA (stock=10 mg/ml) was added to a final concentration of 0.1 mg/ml.

The activation buffer was made of 100 μg/ml of calf thymus DNA in control buffer (10 mM Tris-HCl (pH 7.4), 1 mM EDTA (pH 8.0)).

Per tube, the reaction mix was composed of: 2.5 μl, of activation or control buffers, 5 μl of X5 reaction buffer, 2.5 μl of p53-derived biotinylated peptide substrate (stock=4 mM), 0.2 μl of BSA (stock at 10 mg/ml) and 5 μl of [$\gamma$-$^{32}$P] ATP (5 μl of 0.5 mM cold ATP+0.05 μl of Redivue [$\gamma$-$^{32}$P] ATP=Amersham M0068-250 μCi, 3000 Ci/mmol, 10 μCi/μl).

The DNA-PK enzyme (Promega V5811, concentration=100 U/μL) was diluted 1/10 in X1 reaction buffer and kept on ice until imminent use. 10.8 μl of the diluted enzyme was incubated with 1.2 μl, of 100 μM compounds (diluted 1/100 in water from 10 mM stock in neat DMSO) for 10 minutes, at room temperature. During that time, 15.2 μl of the reaction mix was added to screw-capped tubes, behind Perspex glass. 9.8 μl of the enzyme was then transferred to the tubes containing the reaction mix and after 5 minutes incubation, at 30° C., the reaction was stopped by adding 12.5 μl of termination buffer (7.5 M guanidine hydrochloride).

After mixing well, a 10 μl aliquot of each tube was spotted onto a SAM$^{2R}$ biotin capture membrane, which was left to dry for a few minutes. The membrane was then washed extensively to remove the excess free [$\gamma$-$^{32}$P] ATP and nonbiotinylated proteins: once for 30 seconds in 200 ml of 2M NaCl, 3 times for 2 minutes each in 200 ml of 2M NaCl, 4 times for 2 minutes each in 2M NaCl in 1% $H_3PO_4$ and twice for 30 seconds each in 100 ml of deionised water. The membrane was then left to air-dry at room temperature for 30-60 minutes.

Each membrane square was separated using forceps and scissors and placed into a scintillation vial, after which 8 ml of scintillation liquid (Flo-Scint 6013547 from Perkin-Elmer) was added. The amount of $^{32}$P incorporated into the DNA-PK biotinylated peptide substrate was then determined by liquid scintillation counting.

The efficacy of the compounds of the invention in blocking the activation of the PI3K/PKB pathway can be demonstrated in cellular settings as follows:

Protocol for the detection of phospho-PKB and phospho-GSK3β.

On day 1, U87MG cells (ATCC No. HTB-14) are trypsinized, counted in a Neubauer chamber, and diluted in fresh complete RPMI 1640 medium to a final concentration of 6×10$^5$ cells/mL. Ten (10) cm tissue culture dishes are then loaded with 10 mL of the cell suspension, and incubated for 18 hours.

On day 2, the medium in plates is discarded and replaced by complete RPMI 1640 medium containing either DMSO or inhibitors [compounds of formula (I)]. After 30 minutes of contact, the medium is quickly removed by aspiration and the cells rinsed twice with pre-cooled PBS. Cells are then placed on ice and immediately lysed. Protein samples are then resolved by SDS-PAGE and transferred to Immbilon-P membrane for detection of levels of endogenous GSK3β, PKB, PhosphoT308-PKB and PhosphoS9-GSK3β by westernblotting. Membranes are then dried and covered with polyethylene film, and chemiluminescence measured in a MultiImage™ Light Cabinet (Alpha Innotech Corp) driven with the FluorChem™ software (Alpha Innotech Corp).

The data are analyzed with AlphaEasy software, plotted as % of control (cells treated with DMSO in identical experimental conditions used for kinase inhibitors) with SigmaPlot® (SSPI Inc, version 7) as a regression curve (Four Parameter Logistic Cubic) and $IC_{50}$ values are determined accordingly.

There are also experiments to demonstrate the antitumor activity of compounds of the formula (I) in vivo.

Female Harlan athymic nu/nu mice with s.c. transplanted human glioblastoms U87MG tumors can be used to determine the anti-tumor activity of PI3 kinase inhibitors. On day 0, with the animals under peroral forene narcosis, a tumor fragment of approximately 25 mg is placed under the skin on the animals' left flank and the small incised wound is closed by means of suture clips. When tumors reaches a volume of 100 mm$^3$ the mice are divided at random into groups of 6-8 animals and treatment commences. The treatment is carried out for a 2-3 weeks period with peroral, intravenous or intraperitoneal administration once daily (or less frequently) of a compound of formula (I) in a suitable vehicle at defined doses. The tumors are measured twice a week with a slide gauge and the volume of the tumors is calculated.

As an alternative to cell line U87MG, other cell lines may also be used in the same manner, for example, the MDA-MB 468 breast adenocarcinoma cell line (ATCC No. HTB 132; see also In Vitro 14, 911-15 [1978]);

the MDA-MB 231 breast carcinoma cell line (ATCC No. HTB-26; see also In Vitro 12, 331 [1976]);

the MDA-MB 453 breast carcinoma cell line (ATCC No. HTB-131);

the Colo 205 colon carcinoma cell line (ATCC No. CCL 222; see also Cancer Res. 38, 1345-55 [1978]);

the DU145 prostate carcinoma cell line DU 145 (ATCC No. HTB 81; see also Cancer Res. 37, 4049-58 [1978]), the PC-3 prostate carcinoma cell line PC-3 (especially preferred; ATCC No. CRL 1435; see also Cancer Res. 40, 524-34 [1980]) and the PC-3M prostate carcinoma cell line;

the A549 human lung adenocarcinoma (ATCC No. CCL 185; see also Int. J. Cancer 17, 62-70 [1976]), the NCI-H596 cell line (ATCC No. HTB 178; see also Science 246, 491-4 [1989]);

the pancreatic cancer cell line SUIT-2 (see Tomioka et al., Cancer Res. 61, 7518-24 [2001]).

Compounds of the invention exhibit T cell inhibiting activity. More particular the compounds of the invention prevent T cell activation and/or proliferation in e.g. aqueous solution, e.g. as demonstrated in accordance with the following test method. The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice (1.6×105 cells from each strain per well in flat bottom tissue culture microtiter plates, 3.2×105 in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi 3H-thymidine is added.

Cells are harvested after an additional five-hour incubation period, and incorporated 3H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition (IC50 values) are determined. In this assay, the compounds of the invention have IC50 values in the range of 1 nM to 10 µM, preferably from 10 nM to 100 nM.

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer and leucovorin. The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trade-mark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a PI3K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S.

Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt.

Somatostatin receptor antagonists as used herein refers to compounds which target, treat or inhibit the somatostatin receptor such as octreotide, and SOM230.

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term EDG binders as used herein refers a class of immunosuppressants that modulates lymphocyte recirculation, such as FTY720.

The term ribonucleotide reductase inhibitors refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium. Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action. The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

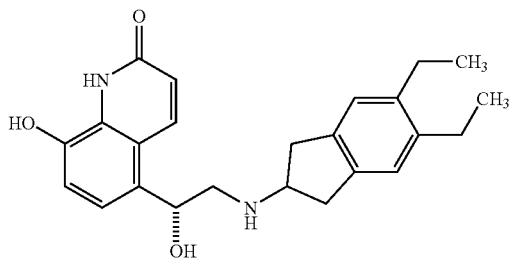

and pharmaceutically acceptable salts thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

The structure of the active compounds identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula (I), can be prepared and administered as described in the art, such as in the documents cited above.

A compound of the formula (I) may also be used to advantage in combination with known therapeutic processes, for example, the administration of hormones or especially radiation. A compound of formula (I) may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g. synergistic effect.

The invention also provides a pharmaceutical preparation, comprising a compound of formula I as defined herein, or an N-oxide or a tautomer thereof, or a pharmaceutically acceptable salt of such a compound, or a hydrate or solvate thereof, and at least one pharmaceutically acceptable carrier.

A compound of formula I can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of formula I can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

The dose of a compound of the formula I or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g, most preferably from about 100 mg to about 1000 mg per person per day, divided preferably into 1 to 3 single doses which may, for example, be of the same size. Usually, children receive half of the adult dose.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned disorders, of a compound of formula I or an N-oxide or a tautomer thereof together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectioning, dissolving or lyophilising processes, and comprise approximately from 1% to 99%, especially from approximately 1% to approximately 20%, active ingredient(s).

Additionally, the present invention provides a compound of formula I or an N-oxide or a tautomer thereof, or a pharmaceutically acceptable salt of such a compound, for use in a method for the treatment of the human or animal body.

The present invention also relates to the use of a compound of formula I or a tautomer thereof, or a pharmaceutically acceptable salt of such a compound, for the preparation of a medicament for the treatment of a proliferative disease, an inflammatory disease, or an obstructive airway disease, or disorders commonly occurring in connection with transplantation.

Furthermore, the invention relates to a method for the treatment of a proliferative disease which responds to an inhibition of lipid kinases and/or PI3-kinase-related protein kinases, in particular the PI3 kinase, and/or DNA protein kinase activity, which comprises administering a compound of formula I or an N-oxide or a tautomer thereof, or a pharmaceutically acceptable salt, or a hydrate or solvate thereof, wherein the radicals and symbols have the meanings as defined above, in a quantity effective against the said disease, to a warm-blooded animal, in particular to humans, requiring such treatment.

Furthermore, the invention relates to a pharmaceutical composition for treatment of solid or liquid tumours in warm-blooded animals, including humans, comprising an antitumourally effective dose of a compound of the formula I as described above or a pharmaceutically acceptable salt of such a compound together with a pharmaceutical carrier.

The invention also provides a process for the preparation of a compound of formula I according to claim 1, or a pharmaceutically acceptable salt thereof, characterized in that a imidazoquinoline derivative of the formula II A compound of the invention may be prepared by processes that, though not applied hitherto for the new compounds of the present invention, are known per se, especially by a process characterized in that for the synthesis of a compound of the formula I wherein the symbols $R_1$, $R_2$, $R_3$, $R_4$, $R_5$, $R_6$ and n are as defined for a compound of the formula I, a compound of the formula II

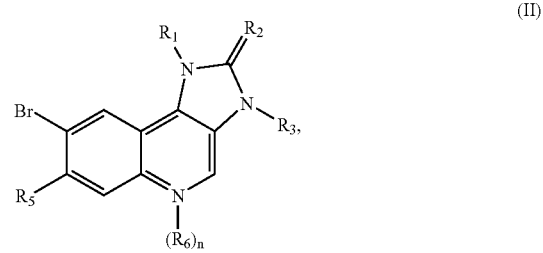

(II)

wherein $R_1$, $R_2$, $R_3$, $R_5$, $R_6$ and n are as defined for a compound of the formula I is reacted with a boronic acid of the formula III $R_4$—$B(OH)_2$ (III)

or of formula IIIa

(IIIa)

wherein $R_4$ is as defined for a compound of the formula I in the presence of a base and a catalyst in a suitable solvent;

where the above starting compounds II and III may also be present with functional groups in protected form if necessary and/or in the form of salts, provided a salt-forming group is present and the reaction in salt form is possible;

any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

DETAILED DESCRIPTION OF THE PROCESS

In the more detailed description of the process below, $R_1$, $R_2$, $R_3$, $R_4$, $R_5$, $R_6$ and n are as defined for compounds of formula I, unless otherwise indicated.

The reaction of compound of formula II and III is preferably carried out under the conditions of a Suzuki-reaction, preferably in a mixture of a polar aprotic solvent such as DMF and water in the presence of a catalyst, especially a noble metal catalyst, such as palladium (II), preferable bis(triphenylphosphine)palladium (II) dichloride; in the presence of a base such as potassium carbonate.

Protecting Groups

If one or more other functional groups, for example carboxy, hydroxy, amino, or mercapto, are or need to be protected in a compound of formulae II or III, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, N.Y. 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself.

Enantiomers may be separated through the formation of diastereomeric salts, for example by salt formation with an enantiomer-pure chiral acid, or by means of chromatography, for example by HPLC, using chromatographic substrates with chiral ligands.

A compound of the formula I, wherein $R_2$ is O, can be converted into the respective compound wherein $R_2$ is S, for example, by using an appropriate sulfur compound, e.g. using reaction with Lawesson's reagent (2,4-bis-(4-methoxyphenyl)2,4-dithioxo-1,2,3,4-dithiaphosphetan) in an appropriate solvent such as dioxane.

It should be emphasized that reactions analogous to the conversions mentioned in this chapter may also take place at the level of appropriate intermediates.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from –100° C. to about 190° C., preferably from about –80° C. to about 150° C., for example at –80 to –60° C., at room temperature, at –20 to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures, typically as described under "Additional process steps".

The solvents from which those can be selected which are suitable for the reaction in question include for example water, esters, typically lower alkyl-lower alkanoates, e.g ethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, 1-butanol, nitriles, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The compounds of formula I, including their salts, are also obtainable in the form of hydrates, or their crystals can include for example the solvent used for crystallization (present as solvates).

In the preferred embodiment, a compound of formula I is prepared according to or in analogy to the processes and process steps defined in the Examples.

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the formula II and III are known, commercially available, or can be synthesized in analogy to or according to methods that are known in the art.

For example, a compound of the formula II, wherein n is 0, can be prepared by the alkylation of an amino compound of the formula IV,

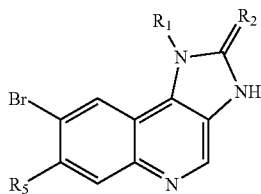

(IV)

wherein $R_1$, $R_2$ and $R_5$ have the meanings as given under formula I with a compound of the formula V

$R_3$—X  (V)

wherein $R_3$ has the meaning as given under formula I and X is halogen or another suitable leaving group, in the presence of a base, e.g. sodium hydroxide, in a suitable solvent, e.g. a mixture of dichloromethane and water, preferably in the presence of a phase transfer catalyst, e.g. tetrabutylammonium bromide, at a temperature between 0° C. and 50° C., preferably at room temperature.

A compound of the formula II, wherein n is 0, can be converted into the respective compound wherein n is 1, for example, by using an appropriate oxidant, e.g. using reaction with meta-chloroperbenzoic acid in an appropriate solvent such as dichloromethan at room temperature.

A compound of the formula IV, wherein $R_2$ is O, can be prepared by the cyclisation of a diamino compound of the formula VI,

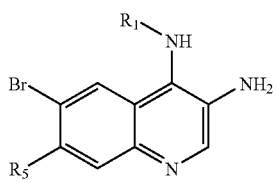

(VI)

wherein $R_1$ and $R_5$ have the meanings as given under formula I with trichloromethyl chloroformate in the presence of a base, such as triethylamine in an appropriate solvent, such as dichloromethane.

A compound of the formula VI can be prepared by the reduction of a nitro compound of the formula VII,

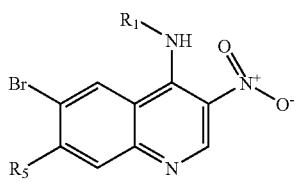

(VII)

wherein $R_1$ and $R_5$ have the meanings as given under formula I.

The reduction preferably takes place in the presence of a suitable reducing agent, such as hydrogen in the presence of an appropriate catalyst, such as Raney nickel under pressure, e.g. between 1.1 and 2 bar, in an appropriate solvent, e.g. an alcohol or ether, such as methanol or tetrahydrofurane or a mixture thereof. The reaction temperature is preferably between 0 and 80° C., especially 15 to 30° C.

A compound of the formula VII can be prepared by reaction of a compound VIII

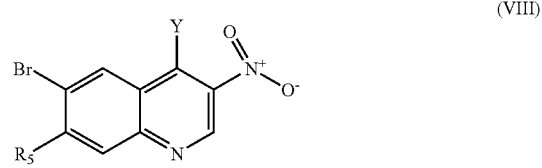

(VIII)

wherein $R_5$ is as defined for a compound of the formula I and Y is halogen or another suitable leaving group, is reacted with a compound of the formula IX,

$R_1$—$NH_2$  (IX)

wherein $R_1$ is as defined for a compound of the formula I, at a temperature between 0° C. and 50° C., preferably at room temperature in a suitable solvent, i.e. acetic acid.

All remaining starting materials such as starting materials of the formula III, IV and V are known, capable of being prepared according to known processes, or commercially obtainable; in particular, they can be prepared using processes as described in the Examples.

Abbreviations:

EtOAc ethyl acetate

Me methyl m.p. melting point

Boc tert-butoxycarbonyl conc. concentrated

DMF N,N-dimethylformamide

ES-MS electrospray mass spectrometry

Grad gradient h hour(s)

HPLC high-pressure liquid chromatography l litre(s)

min minute(s)

MS mass spectrum

Prep. HPLC preparative HPLC reverse phase C18 sat. saturated rt room temperature $t_{ret}$ HPLC retention time in min

TFA trifluoroacetic acid

THF tetrahydrofurane

The following Examples serve to illustrate the invention without limiting the invention in its scope.

Temperatures are measured in degrees celsius (° C.). Unless otherwise indicated, the reactions take place at room temperature (RT).

Ratios of solvents (e.g. in eluents or solvent mixtures) are given in volume by volume (v/v).

HPLC linear gradient between A=H₂O/TFA 1000:1 and B=acetonitrile/TFA 1000:1 Grad 1: 2-100% B in 4.5 min and 1 min at 100% B; column: Chromolith Performance 100 mm×4.5 mm (Merck, Darmstadt, Germany); flow rate 2 ml/min. Detection at 215 nM Grad 2: 2-100% B in 5 minutes and 2 minutes at 100% B; column: Nucleosil $C_{18}$ reverse phase; 150 mm×4.6 mm (SMT, Burkard Instruments, Dietikon, Switzerland); flow rate: 2.0 ml/min. Detection at 215 nm.

Example 1

2-Methyl-2-[4-(3-methyl-2-oxo-8-pyridin-4-yl-2,3-dihydro-imidazo[4,5-c]quinolin-1-yl)-phenyl]-propionitrile

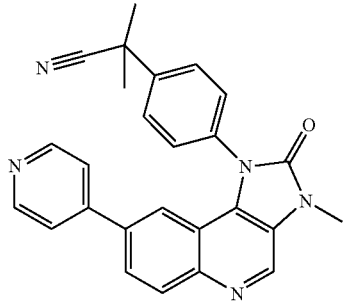

37 mg (0.3 mmol) of 4-pyridineboronic acid (Aldrich, Buchs, Switzerland), 8 mg of bis(triphenylphosphine)palladium (II) dichloride (Fluka, Buchs, Switzerland) and 0.5 ml of a 1 M solution of Na₂CO₃ are added to a solution of 84 mg (0.2 mmol) of 2-[4-(8-bromo-3-methyl-2-oxo-2,3-dihydro-imidazo[4,5-c]quinolin-1-yl)-phenyl]-2-methyl-propionitrile (Example 1i) in 2 ml of DMF. The mixture is stirred for 1 h at 100° C. After this time, the mixture is quenched with sat. aqueous NaHCO₃ and extracted with EtOAc (2×). The organic layer is washed with brine, dried over Na₂SO₄, filtered and evaporated in vacuo. The residue is loaded on silica gel and purified by flash chromatography (CH₂Cl₂-MeOH 97:3 to 18:1) to give the title compound as an off-white solid. ES-MS: 420 (M+H)⁺; analytical HPLC: $t_{ret}$=2.40 min (Grad 1).

Example 1a

5-Bromo-2-(2-nitro-vinylamino)-benzoic acid

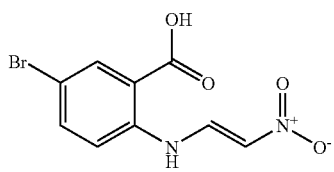

A suspension of 25 g (16 mmol) of 2-amino-5-bromo-benzoic acid (Fluka, Buchs, Switzerland) in H₂O—HCl (37%) (10:1) is stirred for 8 h and then filtered (solution A). 8.17 g (255 mmol) of nitromethane (Fluka, Buchs, Switzerland) are added over 10 min to an ice-bath cooled mixture of 35 g of ice and 15.3 g (382 mmol) of NaOH. After stirring for 1 h at 0° C. and 1 h at rt, the solution is added at 0° C. to 28 g of ice and 42 ml of HCl (37%) (solution B). Solutions A and B are combined and the reaction mixture is stirred for 18 h at rt. The yellow precipitate is filtered off, washed with H₂O and dried in vacuo at 40° C. to give the title compound. ES-MS: 287, 289 (M+H)⁺, Br pattern; ¹H NMR (DMSO-d₆): δ 13.7-14.6/br s (1H), 12.94/d (1H), 8.07/d (1H), 8.03/dd (1H), 7.83/dd (1H), 7.71/d (1H), 6.76/d (1H).

Example 1b

6-Bromo-3-nitro-quinolin-4-ol

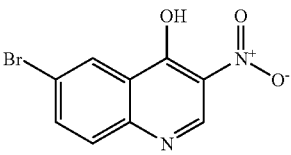

29 g (101 mmol) of 5-bromo-2-(2-nitro-vinylamino)-benzoic acid (Example 1a) and 11.9 g (121 mmol) of potassium acetate in 129 ml (152 mmol) of acetic anhydride are stirred for 1.5 h at 120° C. The precipitate is filtered off and washed with acetic acid until the filtrate is colorless, then is washed with H₂O and dried in vacuo to give the title compound. ES-MS: 269, 271 (M+H)⁺, Br pattern; analytical HPLC: $t_{ret}$=2.70 min (Grad 1).

Example 1c

6-Bromo-4-chloro-3-nitro-quinoline

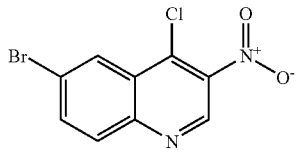

20 g (74.3 mmol) of 6-bromo-3-nitro-quinolin-4-ol (Example 1b) in 150 ml (1.63 mol) of POCl₃ are stirred for 45 min at 120° C. The mixture is cooled to rt and poured slowly into ice-water. The precipitate is filtered off, washed with ice-cold water, and dissolved in CH₂Cl₂. The organic phase is washed with cold brine, and the aqueous phase is discarded. After drying over MgSO₄, the organic solvent is evaporated to dryness to provide the title compound. ¹H NMR (CDCl₃): δ 9.20/s (1H), 8.54/d (1H), 8.04/d (1H), 7.96/dd (1H); analytical HPLC: $t_{ret}$=4.32 min (Grad 1).

Example 1d

2-Methyl-2-(4-nitro-phenyl)-propionitrile

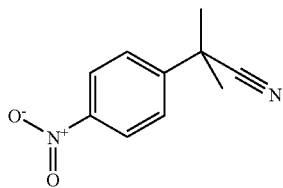

To 15 g (92.5 mmol) of (4-nitro-phenyl)-acetonitrile (Fluka, Buchs, Switzerland), 1.64 mg (5.09 mmol) of tetrabutylammonium bromide (Fluka, Buchs, Switzerland) and 43.3 g (305 mmol) of iodomethane in 125 mL of CH₂Cl₂ are added 10 g (250 mmol) of NaOH in 125 ml of water. The reaction mixture is stirred for 20 h at RT. After this time, the organic layer is separated, dried over MgSO₄, and evaporated to dryness. The residue is dissolved in diethylether and treated with black charcoal for 30 min, filtered over Celite and evaporated in vacuo to give the title compound as a pale yellow solid. Analytical HPLC: $t_{ret}$=3.60 minutes (Grad 1).

Example 1e (2-(4-Amino-phenyl)-2-methyl-propionitrile

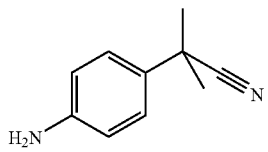

16 g (84.1 mmol) of 2-methyl-2-(4-nitro-phenyl)-propionitrile (Example 1d) and 4.16 g of Raney-Ni are shacked in 160 ml of THF-MeOH (1:1) under 1.1 bar of $H_2$ for 12 h at rt. After completion of the reaction, the catalyst is filtered-off and the filtrate is evaporated to dryness. The residue is purified by flash chromatography on silica gel (hexane-EtOAc 3:1 to 1:2) to provide the title compound as an oil. ES-MS: 161 $(M+H)^+$; analytical HPLC: $t_{ret}$=2.13 minutes (Grad 1).

Example 1f

2-[4-(6-Bromo-3-nitro-quinolin-4-ylamino)-phenyl]-2-methyl-propionitrile

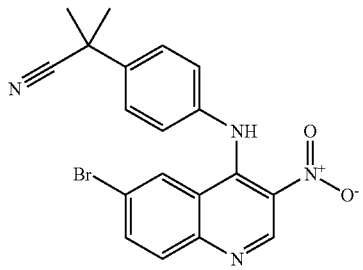

18 g (62.6 mmol) of 6-bromo-4-chloro-3-nitro-quinoline (Example 1c) and 11 g (68.9 mmol) of (2-(4-amino-phenyl)-2-methyl-propionitrile (Example 1e) are dissolved in 350 ml of acetic acid and stirred for 2 h. After this time, water is added and the yellow precipitate is filtered off and washed with $H_2O$. The solid is dissolved in EtOAc-THF (1:1), washed with sat. aqueous $NaHCO_3$ and dried over $MgSO_4$. The organic phase is evaporated to dryness to give the title compound as a yellow solid. ES-MS: 411, 413 $(M+H)^+$, Br pattern; analytical HPLC: $t_{ret}$=3.69 min (Grad 1).

Example 1g

2-[4-(3-Amino-6-bromo-quinolin-4-ylamino)-phenyl]-2-methyl-propionitril

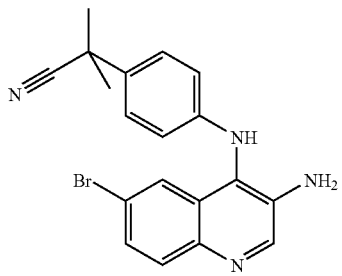

24 g (58.4 mmol) of 2-[4-(6-bromo-3-nitro-quinolin-4-ylamino)-phenyl]-2-methyl-propionitril (Example 1e) is shacked in 300 ml of MeOH-THF (1:1) under 1.1 bar of $H_2$ in the presence of 8.35 g of Raney-Ni for 1 h. After completion of the reaction, the catalyst is filtered off and the filtrate is evaporated to dryness to give the title compound as a yellow foam. ES-MS: 381, 383 $(M+H)^+$, Br pattern; analytical HPLC: $t_{ret}$=3.21 min (Grad 1).

Example 1h

2-[4-(8-Bromo-2-oxo-2,3-dihydro-imidazo[4,5-c]quinolin-1-yl)-phenyl]-2-methyl-propionitrile

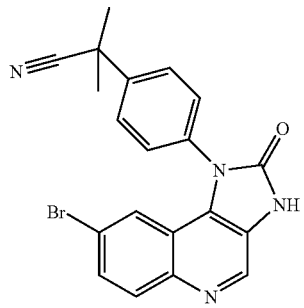

A solution of 5 g (13.1 mmol) of 2-[4-(3-amino-6-bromo-quinolin-4-ylamino)-phenyl]-2-methyl-propionitrile (Example 1g) and 1.59 g (15.7 mmol) of triethylamine in 120 ml $CH_2Cl_2$ is added over 40 min to a solution of 2.85 g (14.4 mmol) of trichloromethyl chloroformate (Fluka, Buchs, Switzerland) in 80 ml of $CH_2Cl_2$ at 0° C. with an ice-bath. The reaction mixture is stirred for 20 min at this temperature then is quenched with sat. aqueous $NaHCO_3$, stirred for 5 min and extracted with $CH_2Cl_2$. The organic layer is dried over $Na_2SO_4$, filtered and evaporated in vacuo to give crude title compound as a brownish solid. ES-MS: 407, 409 $(M+H)^+$, Br pattern; analytical HPLC: $t_{ret}$=3.05 min (Grad 1).

Example 1i

2-[4-(8-Bromo-3-methyl-2-oxo-2,3-dihydro-imidazo[4,5-c]quinolin-1-yl)-phenyl]-2-methyl-propionitrile

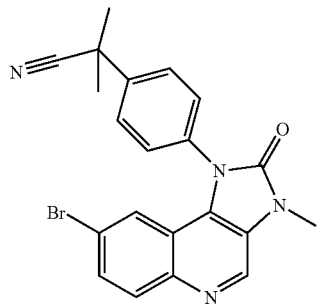

To a solution of 3.45 g (8.47 mmol) of 2-[4-(8-bromo-2-oxo-2,3-dihydro-imidazo[4,5-c]quinolin-1-yl)-phenyl]-2-methyl-propionitrile (Example 1h), 1.8 g (12.7 mmol) of iodomethane (Fluka, Buchs, Switzerland) and 273 mg (0.847 mmol) of tetrabutylammonium bromide (Fluka, Buchs, Switzerland) in 170 ml of $CH_2Cl_2$ is added a solution of 508 mg (12.7 mmol) of NaOH (Fluka, Buchs, Switzerland) in 85 ml of $H_2O$. The reaction mixture is stirred for 2 days and 900 mg (6.35 mmol) of iodomethane and 254 mg (6.35 mmol) of NaOH in 5 ml of $H_2O$ are added. The reaction mixture is stirred for 1 day at rt. After this time, the reaction is quenched with $H_2O$ and extracted with $CH_2Cl_2$ (2×). The organic layer is washed with brine, dried over Na$_2$SO$_4$, filtered and evaporated in vacuo to give the title compound as a beige solid. ES-MS: 421, 423 (M+H)$^+$, Br pattern; analytical HPLC: t$_{ret}$=3.15 min (Grad 1).

The following compounds (Table 1) are prepared in a similar manner as described in example 1 by reacting 2-[4-(8-bromo-3-methyl-2-oxo-2,3-dihydro-imidazo[4,5-c]quinolin-2-yl)-phenyl]-2-methyl-propionitrile (Example 1i), with the appropriate boronic acid:

Example 2

3-pyridineboronic acid (Aldrich, Buchs, Switzerland),

Example 3

4-methoxy-3-pyridylboronic acid (Frontier Scientific, Logan, USA),

Example 4

3-methoxypyridine-5-boronic acid pinecol ester (Frontier Scientific, Logan, USA)

Example 5

4-[5-(4,4,5,5-Tetramethyl-[1,3,2]dioxaborolan-2-yl)-pyridin-2-yl]-piperazine-1-carboxylic acid tert-butyl ester (CB Research & Development, New Castle, USA)

Example 6

1-Methyl-4-[4-(4,4,5,5-tetramethyl-[1,3,2]dioxaborolan-2-yl)-pyridin-2-yl]-piperazine (Oakwood Products, West Columbia, USA), Example 7

3-quinolineboronic acid (Aldrich, Buchs, Switzerland),

Example 8

2-fluoroquinoline-3-boronic acid (Lancaster, Morecambe, UK),

Example 9

6-quinolineboronic acid (Asychem, Durham, USA),

Example 10

5-quinolineboronic acid (Asychem, Durham, USA), and

Example 11

6-benzopyrazineboronic acid hydrochloride (Asychem, Durham, USA)

TABLE 1

| Example | Compound name | ES-MS (M + H)$^+$ | t$_{ret}$ [min] |
|---|---|---|---|
| 2 | 2-Methyl-2-[4-(3-methyl-2-oxo-8-pyridin-3-yl-2,3-dihydro-imidazo[4,5-c]quinolin-1-yl)-phenyl]-propionitrile | 420 | 2.44 Grad 1 |
| 3 | 2-{4-[8-(6-Methoxy-pyridin-3-yl)-3-methyl-2-oxo-2,3-dihydro-imidazo[4,5-c]quinolin-1-yl]-phenyl}-2-methyl-propionitrile | 450.3 | 4.63 Grad 2 |
| 4 | 2-{4-[8-(5-Methoxy-pyridin-3-yl)-3-methyl-2-oxo-2,3-dihydro-imidazo[4,5-c]quinolin-1-yl]-phenyl}-2-methyl-propionitrile | 450.3 | 4.12 Grad 2 |
| 5 | 2-Methyl-2-{4-[3-methyl-2-oxo-8-(6-piperazin-1-yl-pyridin-3-yl)-2,3-dihydro-imidazo[4,5-c]quinolin-1-yl]-phenyl}-propionitrile | 504 | 2.45 Grad 1 |
| 6 | 2-Methyl-2-(4-{3-methyl-8-[2-(4-methyl-piperazin-1-yl)-pyridin-4-yl]-2-oxo-2,3-dihydro-imidazo[4,5-c]quinolin-1-yl}-phenyl)-propionitrile | 518 | 2.51 Grad 1 |
| 7 | 2-Methyl-2-[4-(3-methyl-2-oxo-8-quinolin-3-yl-2,3-dihydro-imidazo[4,5-c]quinolin-1-yl)-phenyl]-propionitrile | 470 | 2.90 Grad 1 |
| 8 | 2-{4-[8-(2-Fluoro-quinolin-3-yl)-3-methyl-2-oxo-2,3-dihydro-imidazo[4,5-c]quinolin-1-yl]-phenyl}-2-methyl-propionitrile | 488.4 | 4.82 Grad 2 |
| 9 | 2-Methyl-2-[4-(3-methyl-2-oxo-8-quinolin-6-yl-2,3-dihydro-imidazo[4,5-c]quinolin-1-yl)-phenyl]-propionitrile | 470 | 2.61 Grad 1 |
| 10 | 2-Methyl-2-[4-(3-methyl-2-oxo-8-quinolin-5-yl-2,3-dihydro-imidazo[4,5-c]quinolin-1-yl)-phenyl]-propionitrile | 470 | 2.53 Grad 1 |
| 11 | 2-Methyl-2-[4-(3-methyl-2-oxo-8-quinoxalin-6-yl-2,3-dihydro-imidazo[4,5-c]quinolin-1-yl)-phenyl]-propionitrile | 471 | 3.04 Grad 1 |

The following compounds (Table 2) are prepared in a similar manner as described in Example 1 by reacting 6-bromo-4-chloro-3-nitro-quinoline (Example 1c) with 2-(4-amino-phenyl)-2-ethyl-butyronitrile (Example 12a), and with the appropriate boronic acid:

TABLE 2

| Example | Compound name | ES-MS (M + H)+ | $t_{ret}$ [min] |
|---|---|---|---|
| 12 | 2-Ethyl-2-[4-(3-methyl-2-oxo-8-pyridin-3-yl-2,3-dihydro-imidazo[4,5-c]quinolin-1-yl)-phenyl]-butyronitrile | 448 | 2.69 Grad 1 |
| 13 | 2-Ethyl-2-[4-(3-methyl-2-oxo-8-quinolin-3-yl-2,3-dihydro-imidazo[4,5-c]quinolin-1-yl)-phenyl]-butyronitrile | 498 | 3.13 Grad 1 |

Example 12a 2-(4-Amino-phenyl)-2-ethyl-butyronitrile

The title compound is prepared in a similar manner as described in Example 1e using iodoethane (Fluka, Buchs, Switzerland) in Example 1d. Title compound: ES-MS: 189 (M+H)+, Br pattern; analytical HPLC: $t_{ret}$=2.50 min (Grad 1).

The following compounds (Table 3) are prepared in a similar manner as described in Example 1 by reacting 6-bromo-4-chloro-3-nitro-quinoline (Example 1c) with 1-(4-amino-2-fluoro-phenyl)-pyrrolidin-2-one (Example 14a), and with the appropriate boronic acid:

TABLE 3

| Example | Compound name | ES-MS (M + H)+ | $t_{ret}$ [min] |
|---|---|---|---|
| 14 | 1-[3-Fluoro-4-(2-oxo-pyrrolidin-1-yl)-phenyl]-3-methyl-8-pyridin-3-yl-1,3-dihydro-imidazo[4,5-c]quinolin-2-one | 454 | 2.26 Grad 1 |
| 15 | 1-[3-Fluoro-4-(2-oxo-pyrrolidin-1-yl)-phenyl]-3-methyl-8-quinolin-3-yl-1,3-dihydro-imidazo[4,5-c]quinolin-2-one | 504 | 2.63 Grad 1 |

Example 14a 1-(4-Amino-2-fluoro-phenyl)-pyrrolidin-2-one 650 mg (2.9 mmol) of 1-(2-fluoro-4-nitro-phenyl)-pyrrolidin-2-one (Example 14b) and 65 mg of Pd/C 10% are shacked in 15 ml of MeOH/THF (1:1) under 1.1 bar of H₂ for 2 h at rt. After completion of the reaction, the catalyst is filtered-off and the filtrate is evaporated in vacuo to give the title compound as an off-white solid. ES-MS: 195 (M+H)+; analytical HPLC: $t_{ret}$=1.91 minutes (Grad 1).

Example 14b 1-(2-Fluoro-4-nitro-phenyl)-pyrrolidin-2-one

To 468 mg (5.5 mmol) of 2-pyrrolidone (Fluka, Buchs, Switzerland) in 10 ml of DMF at 0° C. are added 240 mg (5.5 mmol) of 55% NaH in oil. The reaction mixture is stirred for 30 min at 0° C. and for 30 min at rt. After this time, 795 mg (5 mmol) of 3,4-difluoronitrobenzene (Aldrich, Buchs, Switzerland) are added and the reaction mixture is stirred for 1 h at rt.

The reaction mixture is quenched with 1 M aqueous HCl and extracted with EtOAc (2×). The organic layers are washed with aqueous sat. NaHCO₃ and with brine (3×), dried over MgSO₄, filtered and evaporated. The residue is purified by flash chromatography on silica gel (hexane-EtOAc 5:1 to 1:3) to give the title compound as a solid. ES-MS: 225 (M+H)+; analytical HPLC: $t_{ret}$=2.99 minutes (Grad 1).

The following compounds (Table 4) are prepared in a similar manner as described in Example 1 by reacting 6-bromo-4-chloro-3-nitro-quinoline (Example 1c) with 1-(4-amino-phenyl)-pyrrolidin-2-one (Example 16a), and with the appropriate boronic acid:

TABLE 4

| Example | Compound name | ES-MS (M + H)+ | $t_{ret}$ [min] |
|---|---|---|---|
| 16 | 3-Methyl-1-[4-(2-oxo-pyrrolidin-1-yl)-phenyl]-8-pyridin-3-yl-1,3-dihydro-imidazo[4,5-c]quinolin-2-one | 436 | 2.24 Grad 1 |
| 17 | 3-Methyl-1-[4-(2-oxo-pyrrolidin-1-yl)-phenyl]-8-quinolin-3-yl-1,3-dihydro-imidazo[4,5-c]quinolin-2-one | 486 | 2.61 Grad 1 |

Example 16a 1-(4-Amino-phenyl)-pyrrolidin-2-one

The title compound is obtained in a similar manner as described in Example 14a starting with 1-(4-nitro-phenyl)-pyrrolidin-2-one (Acros, Basel, Switzerland). Title compound: ES-MS: 177 (M+H)+; analytical HPLC: $t_{ret}$=2.71 minutes (Grad 1).

The following compounds (Table 5) are prepared in a similar manner as described in Example 1 by reacting 6-bromo-4-chloro-3-nitro-quinoline (Example 1c) with 2-fluoro-N1,N1-bis-(2-methoxy-ethyl)-benzene-1,4-diamine (Example 18a), and with the appropriate boronic acid:

TABLE 5

| Example | Compound name | ES-MS (M + H)+ | $t_{ret}$ [min] |
|---|---|---|---|
| 18 | 1-{4-[Bis-(2-methoxy-ethyl)-amino]-3-fluoro-phenyl}-3-methyl-8-pyridin-3-yl-1,3-dihydro-imidazo[4,5-c]quinolin-2-one | 502 | 2.53 Grad 1 |
| 19 | 1-{4-[Bis-(2-methoxy-ethyl)-amino]-3-fluoro-phenyl}-3-methyl-8-quinolin-3-yl-1,3-dihydro-imidazo[4,5-c]quinolin-2-one | 552 | 2.96 Grad 1 |

Example 18a

2-Fluoro-N1,N1-bis-(2-methoxy-ethyl)-benzene-1,4-diamine

The title compound is obtained in a similar manner as described in Example 14a starting with (2-fluoro-4-nitrophenyl)-bis-(2-methoxy-ethyl)-amine (Example 18b). Title compound: ES-MS: 243 (M+H)⁺; analytical HPLC: $t_{ret}$=1.98 minutes (Grad 1).

Example 18b (2-Fluoro-4-nitro-phenyl)-bis-(2-methoxy-ethyl)-amine 1.13 g (7.1 mmol) of 3,4-difluoronitrobenzene (Aldrich, Buchs, Switzerland), 1.04 g (7.81 mmol) of bis(2-methoxy-ethyl)amine (Fluka, Buchs, Switzerland) and 1.96 g (14.2 mmol) of $K_2CO_3$ in 7 ml of DMSO are stirred for 1.5 h at rt and then heated at 80° C. for 4 h. The reaction mixture is quenched with $H_2O$ and extracted with EtOAc (2×). The organic layers are washed with brine (3×), dried over $MgSO_4$, filtered and evaporated. The residue is purified by flash chromatography on silica gel (hexane-EtOAc 6:1 to 5:1) to give the title compound as a yellow oil. ES-MS: 273 (M+H)⁺.

The following compounds (Table 6) are prepared in a similar manner as described in Example 1 by reacting 6-bromo-4-chloro-3-nitro-quinoline (Example 1c) with N,N-bis-(2-methoxy-ethyl)-benzene-1,4-diamine (Example 20a), and with the appropriate boronic acid:

TABLE 6

| Example | Compound name | ES-MS (M + H)⁺ | $t_{ret}$ [min] |
|---|---|---|---|
| 20 | 1-{4-[Bis-(2-methoxy-ethyl)-amino]-phenyl}-3-methyl-8-pyridin-3-yl-1,3-dihydro-imidazo[4,5-c]quinolin-2-one | 484 | 2.50 Grad 1 |
| 21 | 1-{4-[Bis-(2-methoxy-ethyl)-amino]-phenyl}-3-methyl-8-quinolin-3-yl-1,3-dihydro-imidazo[4,5-c]quinolin-2-one | 534 | 2.93 Grad 1 |

Example 20a

N,N-Bis-(2-methoxy-ethyl)-benzene-1,4-diamine

The title compound is obtained in a similar manner as in Example 18b starting with 4-fluoronitrobenzene (Aldrich, Buchs, Switzerland). Title compound: ES-MS: 225 (M+H)⁺; analytical HPLC: $t_{ret}$=1.94 minutes (Grad 1).

The following compounds (Table 7) are prepared in a similar manner as described in Example 1 by reacting 6-bromo-4-chloro-3-nitro-quinoline (Example 1c) with 2-naphthylamine (Aldrich, Buchs, Switzerland), and with the appropriate boronic acid:

TABLE 7

| Example | Compound name | ES-MS (M + H)⁺ | $t_{ret}$ [min] |
|---|---|---|---|
| 22 | 3-Methyl-1-naphthalen-2-yl-8-pyridin-3-yl-1,3-dihydro-imidazo[4,5-c]quinolin-2-one | 403 | 2.53 Grad 1 |
| 23 | 3-Methyl-1-naphthalen-2-yl-8-quinolin-3-yl-1,3-dihydro-imidazo[4,5-c]quinolin-2-one | 453 | 3.02 Grad 1 |

The following compounds (Table 8) are prepared in a similar manner as described in Example 1 by reacting 6-bromo-4-chloro-3-nitro-quinoline (Example 1c) with 2-chloroaniline (Fluka, Buchs, Switzerland), and with the appropriate boronic acid:

TABLE 8

| Example | Compound name | ES-MS (M + H)⁺ | $t_{ret}$ [min] |
|---|---|---|---|
| 24 | 1-(2-Chloro-phenyl)-3-methyl-8-pyridin-3-yl-1,3-dihydro-imidazo[4,5-c]quinolin-2-one | 387 | 2.32 Grad 1 |
| 25 | 1-(2-Chloro-phenyl)-3-methyl-8-quinolin-3-yl-1,3-dihydro-imidazo[4,5-c]quinolin-2-one | 437 | 2.83 Grad 1 |

The following compounds (Table 9) are prepared in a similar manner as described in Example 1 by reacting 6-bromo-4-chloro-3-nitro-quinoline (Example 1c) with 2-toluidine (Fluka, Buchs, Switzerland), and with the appropriate boronic acid:

TABLE 9

| Example | Compound name | ES-MS (M + H)⁺ | $t_{ret}$ [min] |
|---|---|---|---|
| 26 | 3-Methyl-8-pyridin-3-yl-1-o-tolyl-1,3-dihydro-imidazo[4,5-c]quinolin-2-one | 367 | 2.27 Grad 1 |
| 27 | 3-Methyl-8-quinolin-3-yl-1-o-tolyl-1,3-dihydro-imidazo[4,5-c]quinolin-2-one | 417 | 2.79 Grad 1 |

The following compounds (Table 10) are prepared in a similar manner as described in Example 1 by reacting 6-bromo-4-chloro-3-nitro-quinoline (Example 1c) with 2-ethylaniline (Aldrich, Buchs, Switzerland), and with the appropriate boronic acid:

TABLE 10

| Example | Compound name | ES-MS (M + H)⁺ | $t_{ret}$ [min] |
|---|---|---|---|
| 28 | 1-(2-Ethyl-phenyl)-3-methyl-8-pyridin-3-yl-1,3-dihydro-imidazo[4,5-c]quinolin-2-one | 381 | 2.40 Grad 1 |
| 29 | 1-(2-Ethyl-phenyl)-3-methyl-8-quinolin-3-yl-1,3-dihydro-imidazo[4,5-c]quinolin-2-one | 431 | 2.93 Grad 1 |

The following compounds (Table 11) are prepared in a similar manner as described in Example 1 by reacting 6-bromo-4-chloro-3-nitro-quinoline (Example 1c) with 2-trifluoromethylaniline (Fluka, Buchs, Switzerland), and with the appropriate boronic acid:

TABLE 11

| Example | Compound name | ES-MS (M + H)⁺ | $t_{ret}$ [min] |
|---|---|---|---|
| 30 | 3-Methyl-8-pyridin-3-yl-1-(2-trifluoromethyl-phenyl)-1,3-dihydro-imidazo[4,5-c]quinolin-2-one | 421 | 2.43 Grad 1 |
| 31 | 3-Methyl-8-quinolin-3-yl-1-(2-trifluoromethyl-phenyl)-1,3-dihydro-imidazo[4,5-c]quinolin-2-one | 471 | 2.91 Grad 1 |

The following compounds (Table 12) are prepared in a similar manner as described in Example 1 by reacting 6-bromo-4-chloro-3-nitro-quinoline (Example 1c) with 4-fluoro-2-methylaniline (Aldrich, Buchs, Switzerland), and with the appropriate boronic acid:

TABLE 12

| Example | Compound name | ES-MS (M + H)+ | t_ret [min] |
|---|---|---|---|
| 32 | 1-(4-Fluoro-2-methyl-phenyl)-3-methyl-8-quinolin-3-yl-1,3-dihydro-imidazo[4,5-c]quinolin-2-one | 385 | 2.30 Grad 1 |
| 33 | 1-(4-Fluoro-2-methyl-phenyl)-3-methyl-8-quinolin-3-yl-1,3-dihydro-imidazo[4,5-c]quinolin-2-one | 435 | 2.85 Grad 1 |

The following compounds (Table 13) are prepared in a similar manner as described in Example 1 by reacting 6-bromo-4-chloro-3-nitro-quinoline (Example 1c) with 2-chloro-4-fluoroaniline (Aldrich, Buchs, Switzerland), and with the appropriate boronic acid:

TABLE 13

| Example | Compound name | ES-MS (M + H)+ | t_ret [min] |
|---|---|---|---|
| 34 | 1-(2-Chloro-4-fluoro-phenyl)-3-methyl-8-pyridin-3-yl-1,3-dihydro-imidazo[4,5-c]quinolin-2-one | 405 | 2.37 Grad 1 |
| 35 | 1-(2-Chloro-4-fluoro-phenyl)-3-methyl-8-quinolin-3-yl-1,3-dihydro-imidazo[4,5-c]quinolin-2-one | 455 | 2.89 Grad 1 |

The following compounds (Table 14) are prepared in a similar manner as described in Example 1 by reacting 6-bromo-4-chloro-3-nitro-quinoline (Example 1c) with 3-chloroaniline (Fluka, Buchs, Switzerland), and with the appropriate boronic acid:

TABLE 14

| Example | Compound name | ES-MS (M + H)+ | t_ret [min] |
|---|---|---|---|
| 36 | 1-(3-Chloro-phenyl)-3-methyl-8-pyridin-3-yl-1,3-dihydro-imidazo[4,5-c]quinolin-2-one | 387 | 2.37 Grad 1 |
| 37 | 1-(3-Chloro-phenyl)-3-methyl-8-quinolin-3-yl-1,3-dihydro-imidazo[4,5-c]quinolin-2-one | 437 | 2.89 Grad 1 |

The following compounds (Table 15) are prepared in a similar manner as described in Example 1 by reacting 6-bromo-4-chloro-3-nitro-quinoline (Example 1c) with 3-trifluoromethylaniline (Fluka, Buchs, Switzerland), and with the appropriate boronic acid:

TABLE 15

| Example | Compound name | ES-MS (M + H)+ | t_ret [min] |
|---|---|---|---|
| 38 | 3-Methyl-8-pyridin-3-yl-1-(3-trifluoromethyl-phenyl)-1,3-dihydro-imidazo[4,5-c]quinolin-2-one | 421 | 2.53 Grad 1 |
| 39 | 3-Methyl-8-quinolin-3-yl-1-(3-trifluoromethyl-phenyl)-1,3-dihydro-imidazo[4,5-c]quinolin-2-one | 471 | 3.02 Grad 1 |

The following compounds (Table 16) are prepared in a similar manner as described in Example 1 by reacting 6-bromo-4-chloro-3-nitro-quinoline (Example 1c) with 4-methoxymethylaniline (Example 38a), and with the appropriate boronic acid:

TABLE 16

| Example | Compound name | ES-MS (M + H)+ | t_ret [min] |
|---|---|---|---|
| 40 | 1-(4-Methoxymethyl-phenyl)-3-methyl-8-pyridin-3-yl-1,3-dihydro-imidazo[4,5-c]quinolin-2-one | 2.28 | 397 Grad 1 |
| 41 | 1-(4-Methoxymethyl-phenyl)-3-methyl-8-quinolin-3-yl-1,3-dihydro-imidazo[4,5-c]quinolin-2-one | 2.75 | 447 Grad 1 |

Example 40a

4-Methoxymethylaniline

The title compound is known in the literature (described in Journal of Chemical Society. Perkin Trans I, 2001, p. 955). Title compound: ES-MS: 138 (M+H)+; analytical HPLC: $t_{ret}$=1.76 min (Grad 1).

The following compounds (Table 17) are prepared in a similar manner as described in Example 1 by reacting 6-bromo-4-chloro-3-nitro-quinoline (Example 1c) with 2-chloro-4-(2-methoxy-ethyl)-phenylamine (Example 42a), and with the appropriate boronic acid:

TABLE 17

| Example | Compound name | ES-MS (M + H)+ | t_ret [min] |
|---|---|---|---|
| 42 | 1-[2-Chloro-4-(2-methoxy-ethyl)-phenyl]-3-methyl-8-pyridin-3-yl-1,3-dihydro-imidazo[4,5-c]quinolin-2-one | 2.53 | 445 Grad 1 |
| 43 | 1-[2-Chloro-4-(2-methoxy-ethyl)-phenyl]-3-methyl-8-quinolin-3-yl-1,3-dihydro-imidazo[4,5-c]quinolin-2-one | 2.99 | 495 Grad 1 |

Example 42a

2-Chloro-4-(2-methoxy-ethyl)-phenylamine 2 g (13.2 mmol) of 4-(2-methoxy-ethyl)-phenylamine (Example 42b) and 1.85 g (13.9 mmol) of N-chlorosuccinimide (Aldrich, Buchs, Switzerland) in 26 ml of isopropanol are stirred at rt for 30 min. The reaction mixture is evaporated to dryness and the residue is taken in EtOAc. The organic layers is washed with sat. aqueous $NaHCO_3$ (2×), dried over $MgSO_4$, filtered and evaporated. The residue is purified by flash chromatography on silica gel (hexane-EtOAc 5:1 to 2:1) to provide the title compound as an oil. ES-MS: 186 (M+H)+; analytical HPLC: $t_{ret}$=2.42 minutes (Grad 1).

Example 42b 4-(2-Methoxy-ethyl)-phenylamine

The title compound is known in the literature (described in Synthetic communications, 1985, 15, p. 1131). Title compound: ES-MS: 152 (M+H)+; analytical HPLC: $t_{ret}$=1.84 min (Grad 1).

The following compounds (Table 18) are prepared in a similar manner as described in Example 1 by reacting 6-bromo-4-chloro-3-nitro-quinoline (Example 1c) with 4-(2-methoxy-ethyl)-phenylamine (Example 42b), and with the appropriate boronic acid:

TABLE 18

| Example | Compound name | ES-MS (M + H)+ | $t_{ret}$ [min] |
|---|---|---|---|
| 44 | 1-[4-(2-Methoxy-ethyl)-phenyl]-3-methyl-8-quinolin-3-yl-1,3-dihydro-imidazo[4,5-c]quinolin-2-one | 411 | 2.37 Grad 1 |
| 45 | 1-[4-(2-Methoxy-ethyl)-phenyl]-3-methyl-8-pyridin-3-yl-1,3-dihydro-imidazo[4,5-c]quinolin-2-one | 461 | 2.83 Grad 1 |

The following compounds (Table 19) are prepared in a similar manner as described in Example 1 using 2-[4-(8-bromo-3-methyl-2-oxo-5-oxy-2,3-dihydro-imidazo[4,5-c]quinolin-1-yl)-phenyl]-2-methyl-propionitrile (Example 46a) with the appropriate boronic acid:

TABLE 19

| Example | Compound name | ES-MS (M + H)+ | $t_{ret}$ [min] |
|---|---|---|---|
| 46 | 2-Methyl-2-[4-(3-methyl-2-oxo-5-oxy-8-pyridin-3-yl-2,3-dihydro-imidazo[4,5-c]quinolin-1-yl)-phenyl]-propionitrile | 436 | 2.57 Grad 1 |
| 47 | 2-Methyl-2-[4-(3-methyl-2-oxo-5-oxy-8-quinolin-3-yl-2,3-dihydro-imidazo[4,5-c]quinolin-1-yl)-phenyl]-propionitrile | 486 | 3.11 Grad 1 |

Example 46a

2-[4-(8-Bromo-3-methyl-2-oxo-5-oxy-2,3-dihydro-imidazo[4,5-c]quinolin-1-yl)-phenyl]-methyl-propionitrile 880 mg (2.09 mmol) of 2-[4-(8-bromo-3-methyl-2-oxo-2,3-dihydro-imidazo[4,5-c]quinolin-1-yl)-phenyl]-2-methyl-propionitrile (Example 1i) and 696 mg (2.3 mmol) of m-chloroperbenzoic acid (Aldrich, Buchs, Switzerland) in 40 ml of $CH_2Cl_2$ are stirred at rt for 2 h. The reaction mixture is quenched with 10% aqueous $Na_2CO_3$ and extracted with $CH_2Cl_2$ (2×). The organic layers are washed with 10% aqueous $Na_2CO_3$ and with brine, dried over $Na_2SO_4$, filtered and evaporated. The residue is triturated in hot EtOAc, then cooled at –18° C. and filtered to give the title compound as a yellow solid. ES-MS: 437, 439 (M+H)+, Br pattern; analytical HPLC: $t_{ret}$=3.45 min (Grad 1).

The following compounds (Table 20) are prepared in a similar manner as described in Example 1 using 6-bromo-4-chloro-7-fluoro-3-nitro-quinoline (Example 48a), and the required boronic acid:

TABLE 20

| Example | Compound name | ES-MS (M + H)+ | $t_{ret}$ [min] |
|---|---|---|---|
| 48 | 2-[4-(7-Fluoro-3-methyl-2-oxo-8-pyridin-3-yl-2,3-dihydro-imidazo[4,5-c]quinolin-1-yl)-phenyl]-2-methyl-propionitrile | 438 | 2.54 Grad 1 |
| 49 | 2-[4-(7-Fluoro-3-methyl-2-oxo-8-quinolin-3-yl-2,3-dihydro-imidazo[4,5-c]quinolin-1-yl)-phenyl]-2-methyl-propionitrile | 488 | 3.03 Grad 1 |

Example 48a 6-bromo-4-chloro-7-fluoro-3-nitro-quinoline

The title compound is prepared in a similar manner as described in Example 1c starting from 2-amino-5-bromo-4-fluoro-benzoic acid (ES-MS: 232, 234 M–H, Br pattern; synthesis described in Macromolecules, 1997, 30, p. 1964). Title compound: analytical HPLC: $t_{ret}$=4.07 min (Grad 1).

Example 50

N-Methyl-N-[4-(3-methyl-2-oxo-8-pyridin-3-yl-2,3-dihydro-imidazo[4,5-c]quinolin-1-yl)-phenyl]-methanesulfonamide 62 mg (0.128 mmol) of methyl-[4-(3-methyl-2-oxo-8-pyridin-3-yl-2,3-dihydro-imidazo[4,5-c]quinolin-1-yl)-phenyl]-carbamic acid tert-butyl ester (Example 50a) is treated with 2.5 ml of 1 M HCl in dioxane at rt for 1 h, and then the solution is evaporated to dryness. The residue is taken in 2 ml of $CH_2Cl_2$ together with 414 µl (5.13 mmol) of pyridine and 66 mg (0.579 mmol) of mesylchloride (Fluka, Buchs, Switzerland). The solution is stirred at rt for 17.5 h, then 15 mg (0.129 mmol) of mesylchloride are added and the reaction mixture is stirred at rt for 5.5 h. The reaction is quenched with sat. aqueous $NaHCO_3$ and extracted with $CH_2Cl_2$ (2×). The organic layers are washed with brine, dried over $Na_2SO_4$, filtered and evaporated. The residue is purified by preparative HPLC to give the title compound as a yellowish solid. ES-MS: 460 (M+H)+; analytical HPLC: $t_{ret}$=2.25 min (Grad 1).

Example 50a

Methyl-[4-(3-methyl-2-oxo-8-pyridin-3-yl-2,3-dihydro-imidazo[4,5-c]quinolin-1-yl)-phenyl]-carbamic acid tert-butyl ester The title compound is prepared in a similar manner as described in Example 1 by reacting 6-bromo-4-chloro-3-nitro-quinoline (Example 1c) with (4-amino-phenyl)-carbamic acid tert-butyl ester (Fluka, Buchs, Switzerland) and using 3-pyrineboronic acid (Aldrich, Buchs, Switzerland). Title compound: ES-MS: 482 (M+H)+; analytical HPLC: $t_{ret}$=2.77 min (Grad 1).

Example 51

Methyl-[4-(3-methyl-2-oxo-8-pyridin-3-yl-2,3-dihydro-imidazo[4,5-c]quinolin-1-yl)-phenyl]-carbamic acid tert-butyl ester The title compound is prepared in a similar manner as described in Example 50 using 3-quinolineboronic acid (Aldrich, Buchs, Switzerland). Title compound: ES-MS: 510 (M+H)+; analytical HPLC: $t_{ret}$=2.65 min (Grad 1).

The following compounds (Table 21) are prepared in a similar manner as described in Example 50 by using ethansulfonyl chloride (Fluka, Buchs, Switzerland) and with the appropriate boronic acid.

TABLE 21

| Example | Compound name | ES-MS (M + H)+ | $t_{ret}$ [min] |
|---|---|---|---|
| 52 | Ethanesulfonic acid methyl-[4-(3-methyl-2-oxo-8-pyridin-3-yl-2,3-dihydro-imidazo[4,5-c]quinolin-1-yl)-phenyl]-amide | 438 | 2.54 Grad 1 |

TABLE 21-continued

| Example | Compound name | ES-MS (M + H)+ | $t_{ret}$ [min] |
|---|---|---|---|
| 53 | Ethanesulfonic acid methyl-[4-(3-methyl-2-oxo-8-quinolin-3-yl-2,3-dihydro-imidazo[4,5-c]quinolin-1-yl)-phenyl]-amide | 488 | 3.03 Grad 1 |

The following compounds (Table 22) are prepared in a similar manner as described in Example 50 by using ethyl-[4-(3-methyl-2-oxo-8-pyridin-3-yl-2,3-dihydro-imidazo[4,5-c]quinolin-1-yl)-phenyl]-carbamic acid tert-butyl ester (ES-MS: 496 (M+H)+; analytical HPLC: $t_{ret}$=2.88 min (Grad 1)) or ethyl-[4-(3-methyl-2-oxo-8-quinolin-3-yl-2,3-dihydro-imidazo[4,5-c]quinolin-1-yl)-phenyl]-carbamic acid tert-butyl ester (ES-MS: 546 (M+H)+; analytical HPLC: $t_{ret}$=3.29 min (Grad 1)), respectively.

TABLE 22

| Example | Compound name | ES-MS (M + H)+ | $t_{ret}$ [min] |
|---|---|---|---|
| 54 | N-Ethyl-N-[4-(3-methyl-2-oxo-8-pyridin-3-yl-2,3-dihydro-imidazo[4,5-c]quinolin-1-yl)-phenyl]-methanesulfonamide | 474 | 2.33 Grad 1 |
| 55 | N-Ethyl-N-[4-(3-methyl-2-oxo-8-quinolin-3-yl-2,3-dihydro-imidazo[4,5-c]quinolin-1-yl)-phenyl]-methanesulfonamide | 524 | 2.72 Grad 1 |

Example 56

2-[4-(3-Ethyl-2-oxo-8-pyridin-3-yl-2,3-dihydro-imidazo[4,5-c]quinolin-1-yl)-phenyl]-2-methyl-propionitrile The title compound is prepared in a similar manner as described in Example 1 by reacting 2-[4-(8-bromo-2-oxo-2,3-dihydro-imidazo[4,5-c]quinolin-1-yl)-phenyl]-2-methyl-propionitrile (Example 1h) with iodoethane (Fluka, Buchs, Switzerland) and using 3-pyridineboronic acid. ES-MS: 434 (M+H)+; analytical HPLC: $t_{ret}$=2.55 min (Grad 1).

Example 57

1-[3-Fluoro-4-(4-methanesulfonyl-piperazin-1-yl)-phenyl]-3-methyl-8-quinolin-3-yl-1,3-dihydro-imidazo[4,5-c]quinolin-2-one The title compound is prepared in a similar manner as described in Example 1 using 3-fluoro-4-(4-methanesulfonyl-piperazin-1-yl)-phenylamine (Example 57a) and 3-quinolineboronic acid. Title compound: ES-MS: 583.5 (M+H)+; analytical HPLC: $t_{ret}$=4.12 minutes (Grad 2).

Example 57a

3-Fluoro-4-(4-methanesulfonyl-piperazin-1-yl)-phenylamine

The title compound is prepared in a similar manner as described in Example 14a using 1-(2-fluoro-4-nitro-phenyl)-4-methanesulfonyl-piperazine (Example 57b). Title compound: ES-MS: 274.3 (M+H)+; analytical HPLC: $t_{ret}$=3.50 minutes (Grad 2).

Example 57b 1-(2-Fluoro-4-nitro-phenyl)-4-methanesulfonyl-piperazine

The title compound is prepared in a similar manner as described in Example 18b using 1-methanesulfonyl-piperazine (ChemBridge Corporation, San Diego, USA). Title compound: ES-MS: 304.3 (M+H)+; analytical HPLC: $t_{ret}$=4.94 minutes (Grad 2).

Example 58

1-[3-Fluoro-4-(4-methanesulfonyl-piperazin-1-yl)-phenyl]-3-methyl-8-pyridin-3-yl-1,3-dihydro-imidazo[4,5-c]quinolin-2-one The title compound is prepared in a similar manner as described in Example 57 using 3-pyridineboronic. Title compound: ES-MS: 533.4 (M+H)+; analytical HPLC: $t_{ret}$=3.75 minutes (Grad 2).

Example 59

1-(3-Fluoro-4-piperazin-1-yl-phenyl)-3-methyl-8-quinolin-3-yl-1,3-dihydro-imidazo[4,5-c]quinolin-2-one The title compound is prepared in a similar manner described in Example 1 using 4-(4-amino-2-fluoro-phenyl)-piperazine-1-carboxylic acid tert-butyl ester (Example 59a) and 3-quinolineboronic acid. The removal of the tert-butoxycarbonyl protecting group is performed by using 4 N HCl in dioxane following protocols known in the art (The peptides, Vol. 3; ed. Edhard Gross and Johannes Meienhofer, Academic Press, New York). Title compound: ES-MS: 505.4 (M+H)+; analytical HPLC: $t_{ret}$=3.63 minutes (Grad 2).

Example 59a 4-(4-amino-2-fluoro-phenyl)-piperazine-1-carboxylic acid tert-butyl ester The title compound is obtained as described in Example 14a using 4-(2-fluoro-4-nitro-phenyl)-piperazine-1-carboxylic acid tert-butyl ester (Example 59b). Title compound: ES-MS: 296.3 (M+H)+; analytical HPLC: $t_{ret}$=4.18 minutes (Grad 2).

Example 59b 4-(2-Fluoro-4-nitro-phenyl)-piperazine-1-carboxylic acid tert-butyl ester The title compound is obtained as described in Example 18b using piperazine-1-carboxylic acid tert-butyl ester (Aldrich, Buchs, Switzerland) and by running the reaction at room temperature. Title compound: ES-MS: 326.3 (M+H)+; analytical HPLC: $t_{ret}$=5.84 minutes (Grad 2).

Example 60

1-(3-Fluoro-4-piperazin-1-yl-phenyl)-3-methyl-8-pyridin-3-yl-1,3-dihydro-imidazo[4,5-c]quinolin-2-one The title compound is prepared as described in Example 59 using 3-pyridineboronic acid. Title compound: ES-MS: 455.4 (M+H)+; analytical HPLC: $t_{ret}$ 3.39 minutes (Grad 2).

Example 61

3-Methyl-1-[4-(4-methyl-piperazin-1-yl)-phenyl]-8-quinolin-3-yl-1,3-dihydro-imidazo[4,5-c]quinolin-2-one The title compound is prepared as described in Example 1 using 4-(4-methyl-piperazin-1-yl)-phenylamine (Acros, Morris Plains, N.J., USA) and 3-quinolineboronic acid. Title compound: ES-MS: 501.5 (M+H)$^+$; analytical HPLC: $t_{ret}$=3.78 minutes (Grad 2).

Example 62

3-Methyl-1-[4-(4-methyl-piperazin-1-yl)-phenyl]-8-pyridin-3-yl-1,3-dihydro-imidazo[4,5-c]quinolin-2-one The title compound is obtained as described in Example 61 using 3-pyridineboronic acid. Title compound: ES-MS: 451.3 (M+H)$^+$; analytical HPLC: $t_{ret}$=3.49 minutes (Grad 2).

Example 63

1-[2-Chloro-4-(4-methyl-piperazin-1-yl)-phenyl]-3-methyl-8-quinolin-3-yl-1,3-dihydro-imidazo[4,5-c]quinolin-2-one The title compound is obtained as described in Example 1 using (6-bromo-3-nitro-quinolin-4-yl)-[2-chloro-4-(4-methyl-piperazin-1-yl)-phenyl]-amine (Example 63a) and 3-quinolineboronic acid. Title compound: ES-MS: 535.4 (M+H)$^+$; analytical HPLC: $t_{ret}$=3.93 minutes (Grad 2).

Example 63a (6-Bromo-3-nitro-quinolin-4-yl)-[2-chloro-4-(4-methyl-piperazin-1-yl)-phenyl]-amine 5 ml of N-methylpiperazine are added to a solution of 600 mg (1.5 mmol) of (6-bromo-3-nitro-quinolin-4-yl)-(2-chloro-4-fluoro-phenyl)-amine (Example 63b) in 2 ml of DMSO. The reaction is heated at 180° C. for 1 h in a microwave oven (Emrys Optimizer, Personal Chemistry). After this time, the solution is concentrated to dryness and the crude compound is purified by preparative MPLC. Title compound: ES-MS: 476.3, 478.3, 480.3 (M+H)$^+$; analytical HPLC: $t_{ret}$=4.28 minutes (Grad 2).

Example 63b (6-Bromo-3-nitro-quinolin-4-yl)-(2-chloro-4-fluoro-phenyl)-amine The title compound is obtained as described in Example 1f using 2-chloro-4-fluoro-phenylamine (Aldrich, Buchs, Switzerland). Title compound: ES-MS: 396.1, 398.1, 400.1 (M+H)$^+$; analytical HPLC: $t_{ret}$=5.69 minutes (Grad 2).

Example 64

1-[2-Chloro-4-(4-methyl-piperazin-1-yl)-phenyl]-3-methyl-8-pyridin-3-yl-1,3-dihydro-imidazo[4,5-c]quinolin-2-one The title compound is obtained as described in Example 63 using 3-pyridineboronic acid. Title compound: ES-MS: 485.3 (M+H)$^+$; analytical HPLC: $t_{ret}$=3.58 minutes (Grad 2).

Example 65

1-[3-Chloro-4-(4-methyl-piperazin-1-yl)-phenyl]-3-methyl-8-quinolin-3-yl-1,3-dihydro-imidazo[4,5-c]quinolin-2-one The title compound is obtained as described in Example 1 using 3-chloro-4-(4-methyl-piperazin-1-yl)-phenylamine (Example 65a) and 3-quinolineboronic acid. Title compound: ES-MS: 536.4 (M+H)$^+$; analytical HPLC: $t_{ret}$=3.78 minutes (Grad 2).

Example 65a

3-Chloro-4-(4-methyl-piperazin-1-yl)-phenylamine 298 mg (0.92 mmol) of [3-chloro-4-(4-methyl-piperazin-1-yl)-phenyl]-carbamic acid tert-butyl ester (Example 65b) are dissolved in 5 ml of 4 N HCl in dioxane. The solution is stirred for 4 h at 50° C., and after this time water is added and the pH is adjusted to 8 with NaHCO$_3$. The suspension is extracted with n-butanol. The organic phase is washed with water, dried over MgSO$_4$ and evaporated to dryness to provide the title compound. Title compound: ES-MS: 226.2 (M+H)$^+$; analytical HPLC: $t_{ret}$=3.09 minutes (Grad 2).

Example 65b

[3-Chloro-4-(4-methyl-piperazin-1-yl)-phenyl]-carbamic acid tert-butyl ester 583 mg (2 mmol) of [4-(4-methyl-piperazin-1-yl)-phenyl]-carbamic acid tert-butyl ester (Example 65c) are dissolved in 10 ml of isopropanol and 286 mg (2.1 mmol) of N-chlorosuccinimide are added. The solution is stirred for 1 h at r.t. and 100 ml of water are added. The suspension is extracted with EtOAc and the organic phase is washed with water, dried over MgSO$_4$ and evaporated to dryness. The residue is purified by MPLC to provide the title compound. Title compound: ES-MS: 326.3 (M+H)$^+$; analytical HPLC: $t_{ret}$=4.43 minutes (Grad 2).

Example 65c

[4-(4-Methyl-piperazin-1-yl)-phenyl]-carbamic acid tert-butyl ester 478 mg (2.5 mmol) of 4-(4-methylpiperazino)aniline (Acros, N.J., USA) are dissolved in 10 ml of THF and 0.67 ml (3 mmol) of Boc$_2$O and 0.49 ml (3.5 ml) of tryethylamine are added. After stirring for 16 h at r.t., the solution is evaporated to dryness and the residue is dissolved in 100 ml of EtOAc. The suspension is washed with water, dried over MgSO$_4$ and evaporated to dryness to provide the title compound. Title compound: ES-MS: 292.2 (M+H)$^+$; analytical HPLC: $t_{ret}$=4.15 minutes (Grad 2).

Example 66

1-[3-Chloro-4-(4-methyl-piperazin-1-yl)-phenyl]-3-methyl-8-pyridin-3-yl-1,3-dihydro-imidazo[4,5-c]quinolin-2-one The title compound is obtained as described in Example 65 using 3-pyridineboronic acid. Title compound: ES-MS: 485.4 (M+H)$^+$; analytical HPLC: $t_{ret}$=3.53 minutes (Grad 2).

Example 67

1-(4-Imidazol-1-yl-2-methyl-phenyl)-3-methyl-8-quinolin-3-yl-1,3-dihydro-imidazo[4,5-c]quinolin-2-one The title compound is obtained as described in Example 1 using 4-imidazol-1-yl-2-methyl-phenylamine (Example 68a) and 3-quinolineboronic acid. Title compound: ES-MS: 483.4 (M+H)$^+$; analytical HPLC: $t_{ret}$=3.78 minutes (Grad 2).

Example 67a

4-Imidazol-1-yl-2-methyl-phenylamine

The title compound is obtained as described in Example 18a/b using 5-fluoro-2-nitrotoluene (Aldrich, Buchs, Switzerland) and 1H-pyrazole (Fluka, Buchs, Switzerland). Title compound: ES-MS: 174.2 (M+H)$^+$; analytical HPLC: $t_{ret}$=3.20 minutes (Grad 2).

Example 68

1-(4-Imidazol-1-yl-2-methyl-phenyl)-3-methyl-8-pyridin-3-yl-1,3-dihydro-imidazo[4,5-c]quinolin-2-one The title compound is obtained as described in Example 67 using 3-pyridineboronic acid. Title compound: ES-MS: 433.3 (M+H)$^+$; analytical HPLC: $t_{ret}$=3.46 minutes (Grad 2).

Example 69

3-Methyl-1-(4-pyrazol-1-yl-phenyl)-8-quinolin-3-yl-1,3-dihydro-imidazo[4,5-c]quinolin-2-one The title compound is obtained as described in Example 1 using 4-pyrazol-1-yl-phenylamine (Example 69a) and 3-quinolineboronic acid. Title compound: ES-MS: 469.4 (M+H)$^+$; analytical HPLC: $t_{ret}$=4.18 minutes (Grad 2).

Example 69a

4-Pyrazol-1-yl-phenylamine

The title compound is obtained as described in Example 18a/b using 1-fluoro-4-nitro-benzene (Fluka, Buchs, Switzerland) and 1H-pyrazole (Fluka, Buchs, Switzerland). Title compound: ES-MS: 160.2 (M+H)$^+$; analytical HPLC: $t_{ret}$=3.61 minutes (Grad 2).

Example 70

3-Methyl-1-(4-pyrazol-1-yl-phenyl)-8-pyridin-3-yl-1,3-dihydro-imidazo[4,5-c]quinolin-2-one The title compound is obtained as described in Example 69 using 3-pyridineboronic acid. Title compound: ES-MS: 419.3 (M+H)$^+$; analytical HPLC: $t_{ret}$=3.80 minutes (Grad 2).

Example 71

3-Methyl-8-quinolin-3-yl-1-(4-[1,2,4]triazol-1-yl-phenyl)-1,3-dihydro-imidazo[4,5-c]quinolin-2-one The title compound is obtained as described in Example 1 using 4-[1,2,4]triazol-1-yl-phenylamine (Example 71a) and 3-quinolineboronic acid. Title compound: ES-MS: 470.3 (M+H)$^+$; analytical HPLC: $t_{ret}$=3.99 minutes (Grad 2).

Example 71a

4-[1,2,4]triazol-1-yl-phenylamine

The title compound is obtained as described in Example 18a/b using 1-fluoro-4-nitro-benzene (Fluka, Buchs, Switzerland) and 1,2,4-triazole (Fluka, Buchs, Switzerland). Title compound: ES-MS: 161.2 (M+H)$^+$; analytical HPLC: $t_{ret}$=3.29 minutes (Grad 2).

Example 72

3-Methyl-8-pyridin-3-yl-1-(4-[1,2,4]triazol-1-yl-phenyl)-1,3-dihydro-imidazo[4,5-c]quinolin-2-one The title compound is obtained as described in Example 71 using 3-pyridineboronic acid. Title compound: ES-MS: 420.3 (M+H)$^+$; analytical HPLC: $t_{ret}$=3.68 minutes (Grad 2).

Example 73

3-Methyl-1-[4-(4-methyl-piperazin-1-yl)-3-trifluoromethyl-phenyl]-8-quinolin-3-yl-1,3-dihydro-imidazo[4,5-c]quinolin-2-one The title compound is obtained as described in Example 1 using 4-(4-methyl-piperazin-1-yl)-3-trifluoromethyl-phenylamine (Example 73a) and 3-quinolineboronic acid. Title compound: ES-MS: 569.5 (M+H)$^+$; analytical HPLC: $t_{ret}$=4.08 minutes (Grad 2).

Example 73a 4-(4-Methyl-piperazin-1-yl)-3-trifluoromethyl-phenylamine

The title compound is obtained as described in Example 18a/b using 2-fluoro-5-nitrobenzotrifluoride (Aldrich, Buchs, Switzerland) and N-methylpyrezarine. Title compound: ES-MS: 260.2 (M+H)$^+$; analytical HPLC: $t_{ret}$=3.59 minutes (Grad 2).

Example 74

3-Methyl-1-[4-(4-methyl-piperazin-1-yl)-3-trifluoromethyl-phenyl]-8-pyridin-3-yl-1,3-dihydro-imidazo[4,5-c]quinolin-2-one The title compound is obtained as described in Example 73 using 3-pyridineboronic acid. Title compound: ES-MS: 519.4 (M+H)$^+$; analytical HPLC: $t_{ret}$=3.78 minutes (Grad 2).

Example 75

1-(3-Chloro-4-piperazin-1-yl-phenyl)-3-methyl-8-quinolin-3-yl-1,3-dihydro-imidazo[4,5-c]quinolin-2-one The title compound is obtained as described in Example 1 using 4-(4-amino-2-chloro-phenyl)-piperazine-1-carboxylic acid tert-butyl ester (Example 75a) and 3-quinolineboronic acid and removal of the tert-butoxycarbonyl protecting group in a similar manner as described in Example 59. Title compound: ES-MS: 521.4 (M+H)$^+$; analytical HPLC: $t_{ret}$=3.68 minutes (Grad 2).

Example 75a 4-(4-Amino-2-chloro-phenyl)-piperazine-1-carboxylic acid tert-butyl ester The title compound is obtained as described in Example 1e using 2-chloro-4-(4-nitro-phenyl)-piperazine-1-carboxylic acid tert-butyl ester (Example 75b) as starting material. Title compound: ES-MS: 312.2, 314.3 (M+H)$^+$; analytical HPLC: $t_{ret}$=4.58 minutes (Grad 2).

Example 75b

2-Chloro-4-(4-nitro-phenyl)-piperazine-1-carboxylic acid tert-butyl ester

To a solution of 1.25 g (4 mmol) of 4-(4-nitro-phenyl)-piperazine-1-carboxylic acid tert-butyl ester (Example 75c) in 10 ml of isopropanol are added 0.72 g (4.2 mmol) of N-chlorosuccinimide. The solution is stirred for 6 h at 50° C. After this time, the solution is evaporated to dryness and the residue is dissolved in 100 ml of EtOAc. The solution is extracted with water, dried over MgSO$_4$ and evaporated to dryness to provide the title compound: ES-MS: 342.2, 344.2 (M+H)$^+$; analytical HPLC: $t_{ret}$=5.70 minutes (Grad 2).

Example 75c 4-(4-Nitro-phenyl)-piperazine-1-carboxylic acid tert-butyl ester To a solution of 0.45 ml (4 mmol) of 4-fluoronitrobenze (Aldrich, Buchs, Switzerland) in 10 ml of DMSO are added 1.12 g (6 mmol) of piperazine-1-carboxylic acid tert-butyl ester (Aldrich, Buchs, Switzerland) and 1.1 g (8 mmol) of K$_2$CO$_3$. The suspension is stirred for 1 h at 100° C. After this time, 100 ml of AcOEt are added and the suspension is extracted with water. The organic solution is dried over MgSO$_4$ and evaporated to dryness to provide the title compound: ES-MS: 307.3 (M+H)$^+$; analytical HPLC: $t_{ret}$=5.72 minutes (Grad 2).

Example 76

1-(3-Chloro-4-piperazin-1-yl-phenyl)-3-methyl-8-pyridin-3-yl-1,3-dihydro-imidazo[4,5-c]quinolin-2-one The title compound is obtained as described in Example 75 using 3-pyridineboronic acid. Title compound: ES-MS: 471.3 (M+H)$^+$; analytical HPLC: $t_{ret}$=3.42 minutes (Grad 2).

Example 77

1-(3-Chloro-4-piperazin-1-yl-phenyl)-8-(6-methoxy-pyridin-3-yl)-3-methyl-1,3-dihydro-imidazo[4,5-c] quinolin-2-one The title compound is obtained as described in Example 75 using 2-methoxy-5-pyridineboronic acid. Title compound: ES-MS: 501.4 (M+H)$^+$; analytical HPLC: $t_{ret}$=3.76 minutes (Grad 2).

Example 78

1-(3-Chloro-4-piperazin-1-yl-phenyl)-8-(5-methoxy-pyridin-3-yl)-3-methyl-1,3-dihydro-imidazo[4,5-c] quinolin-2-one The title compound is obtained as described in Example 75 using 3-Methoxy-5-(4,4,5,5-tetramethyl-[1,3,2]dioxaborolan-2-yl)-pyridine (Frontier Scientific, Logan, USA). Title compound: ES-MS: 501.4 (M+H)$^+$; analytical HPLC: $t_{ret}$=3.55 minutes (Grad 2).

Example 79

8-(6-Methoxy-pyridin-3-yl)-3-methyl-1-[4-(4-methyl-piperazin-1-yl)-3-trifluoromethyl-phenyl]-1,3-dihydro-imidazo[4,5-c]quinolin-2-one The title compound is obtained as described in Example 73 using 2-methoxy-5-pyridineboronic acid. Title compound: ES-MS: 549.2 (M+H)$^+$; analytical HPLC: $t_{ret}$=3.89 minutes (Grad 2).

Example 80

8-(5-Methoxy-pyridin-3-yl)-3-methyl-1-[4-(4-methyl-piperazin-1-yl)-3-trifluoromethyl-phenyl]-1,3-dihydro-imidazo[4,5-c]quinolin-2-one The title compound is obtained as described in Example 73 using 3-methoxy-5-pyridineboronic acid. Title compound: ES-MS: 549.2 (M+H)$^+$; analytical HPLC: $t_{ret}$=3.67 minutes (Grad 2).

Example 81

1-[2-Chloro-4-(4-methyl-piperazin-1-yl)-phenyl]-8-(6-methoxy-pyridin-3-yl)-3-methyl-1,3-dihydro-imidazo[4,5-c]quinolin-2-one The title compound is obtained as described in Example 63 using 2-methoxy-5-pyridineboronic acid. Title compound: ES-MS: 515.4 (M+H)$^+$; analytical HPLC: $t_{ret}$=3.73 minutes (Grad 2).

Example 82

1-[2-Chloro-4-(4-methyl-piperazin-1-yl)-phenyl]-8-(5-methoxy-pyridin-3-yl)-3-methyl-1,3-dihydro-imidazo[4,5-c]quinolin-2-one The title compound is obtained as described in Example 63 using 3-Methoxy-5-(4,4,5,5-tetramethyl-[1,3,2]dioxaborolan-2-yl)-pyridine. Title compound: ES-MS: 515.4 (M+H)$^+$; analytical HPLC: $t_{ret}$=3.58 minutes (Grad 2).

Example 83

1-(3-Chloro-4-piperazin-1-yl-phenyl)-3-methyl-8-quinoxalin-6-yl-1,3-dihydro-imidazo[4,5-c]quinolin-2-one The title compound is obtained as described in Example 75 using benzopyrazine-5-boronic acid HCl (Asymchem, Durham, N.C., USA). Title compound: ES-MS: 522.4 (M+H)$^+$; analytical HPLC: $t_{ret}$=3.70 minutes (Grad 2).

Example 84

3-Methyl-1-(4-piperazin-1-yl-3-trifluoromethyl-phenyl)-8-quinolin-3-yl-1,3-dihydro-imidazo[4,5-c] quinolin-2-one The title compound is obtained as described in Example 1 using 4-(4-amino-2-trifluoromethyl-phenyl)-piperazine-1-carboxylic acid tert-butyl ester (Example 84a). Title compound: Title compound: ES-MS: 555.0 (M+H)$^+$; analytical HPLC: $t_{ret}$=3.86 minutes (Grad 2).

Example 84a 4-(4-Amino-2-trifluoromethyl-phenyl)-piperazine-1-carboxylic acid tert-butyl ester The title compound is obtained as described in Example 1e using 4-(4-nitro-2-trifluoromethyl-phenyl)-piperazine-1-carboxylic acid tert-butyl ester (Example 84b) as starting material. Title compound: ES-MS: 346.2 (M+H)$^+$; analytical HPLC: t$_{ret}$=4.95 minutes (Grad 2).

Example 84b

4-(4-Nitro-2-trifluoromethyl-phenyl)-piperazine-1-carboxylic acid tert-butyl ester The title compound is obtained as described in Example 75c using 1-fluoro-4-nitro-2-trifluoromethyl-benzene as starting material. Title compound: ES-MS: 375.3 (M−H)$^−$.

Example 85

3-Methyl-1-(4-piperazin-1-yl-3-trifluoromethyl-phenyl)-8-pyridin-3-yl-1,3-dihydro-imidazo[4,5-c]quinolin-2-one The title compound is obtained as described in Example 84 using 3-pyridineboronic acid. Title compound: ES-MS: 505.4 (M+H)$^+$; analytical HPLC: t$_{ret}$=3.61 minutes (Grad 2).

Example 86

8-(6-Methoxy-pyridin-3-yl)-3-methyl-1-(4-piperazin-1-yl-3-trifluoromethyl-phenyl)-1,3-dihydro-imidazo[4,5-c]quinolin-2-one The title compound is obtained as described in Example 84 using 2-methoxy-5-pyridineboronic acid. Title compound: ES-MS: 535.4 (M+H)$^+$; analytical HPLC: t$_{ret}$=3.93 minutes (Grad 2).

Example 87

8-(5-Methoxy-pyridin-3-yl)-3-methyl-1-(4-piperazin-1-yl-3-trifluoromethyl-phenyl)-1,3-dihydro-imidazo[4,5-c]quinolin-2-one The title compound is obtained as described in Example 84 using 3-Methoxy-5-(4,4,5,5-tetramethyl-[1,3,2]dioxaborolan-2-yl)-pyridine. Title compound: ES-MS: 535.4 (M+H)$^+$; analytical HPLC: t$_{ret}$=3.71 minutes (Grad 2).

Example 88

3-Methyl-1-(4-piperazin-1-yl-3-trifluoromethyl-phenyl)-8-quinoxalin-6-yl-1,3-dihydro-imidazo[4,5-c]quinolin-2-one The title compound is obtained as described in Example 84 using benzopyrazine-5-boronic acid HCl. Title compound: ES-MS: 556.0 (M+H)$^+$; analytical HPLC: t$_{ret}$=3.92 minutes (Grad 2).

Example 89

1-[3-Chloro-4-(cis-3,5-dimethyl-piperazin-1-yl)-phenyl]-3-methyl-8-pyridin-3-yl-1,3-dihydro-imidazo[4,5-c]quinolin-2-one The title compound is obtained as described in Example 1 using 4-(4-amino-2-chloro-phenyl)-2,6-cis-dimethyl-piperazine-1-carboxylic acid tert-butyl ester (Example 89a) and 3-pyridineboronic acid and removal of the tert-butoxycarbonyl protecting group in a similar manner as described in Example 59. Title compound: ES-MS: 499 (M+H)$^+$; analytical HPLC: t$_{ret}$=2.24 minutes (Grad 1).

Example 89a

4-(4-Amino-2-chloro-phenyl)-2,6-cis-dimethyl-piperazine-1-carboxylic acid tert-butyl ester The title compound is obtained in a similar manner as described in Example 1e starting with 4-(2-chloro-4-nitrophenyl)-2,6-cis-dimethyl-piperazine-1-carboxylic acid tert-butyl ester (Example 89b). Title compound: ES-MS: 340 (M+H)$^+$; analytical HPLC: t$_{ret}$=3.35 minutes (Grad 1).

Example 89b

4-(2-Chloro-4-nitro-phenyl)-2,6-cis-dimethyl-piperazine-1-carboxylic acid tert-butyl ester 983 mg (3.64 mmol) of 1-(2-chloro-4-nitro-phenyl)-3,5-cis-dimethyl-piperazine (Example 89c), 1.59 g (7.29 mmol) Boc-anhydride (Fluka, Buchs, Switzerland) in 5 ml THF and 5.47 ml (5.47 mmol) 1 M aqueous K$_2$CO$_3$ are stirred at rt for 72 h The reaction mixture is quenched with brine and extracted with CH$_2$Cl$_2$ (2×). The combined organic layers are washed with 1 M aqueous HCl, with brine, dried over MgSO$_4$, filtered and evaporated The residue is purified by flash chromatography (CH$_2$Cl$_2$-MeOH 1:0 to 39:1) to give the title compound as a pinkish solid. ES-MS: 370 (M+H)$^+$; analytical HPLC: t$_{ret}$=4.73 minutes (Grad 1).

Example 89c

1-(2-Chloro-4-nitro-phenyl)-3,5-cis-dimethyl-piperazine 1.0 g (5.21 mmol) of 3,4-dichloronitrobenzene (Fluka, Buchs, Switzerland), 624 mg (5.47 mmol) cis-2,6-dimethylpiperazine (Aldrich, Buchs, Switzerland) and 580 mg (5.73 mmol) triethylamine in 20 ml of EtOH are heated in a microwave oven at 170° C. for 6 h and 180° C. for 2 h. The reaction mixture is evaporated to dryness and then taken in EtOAc. The organic layers is extracted with 1 M aqueous HCl(5×) and the combined aqueous layers are basified with NaHCO$_3$ and extracted with CH$_2$Cl$_2$ (3×), washed with brine, dried over MgSO$_4$, filtered and evaporated to dryness to give the title compound as a yellow solid. ES-MS: 270 (M+H)$^+$; analytical HPLC: t$_{ret}$=2.72 minutes (Grad 1).

Example 90

1-[3-Chloro-4-(cis-3,5-dimethyl-piperazin-1-yl)-phenyl]-3-methyl-8-quinolin-3-yl-1,3-dihydro-imidazo[4,5-c]quinolin-2-one The title compound is obtained in a similar manner as described in Example 89 using 3-quinolineboronic acid and removal of the tert-butoxycarbonyl protecting group in a similar manner as described in Example 59. Title compound: ES-MS: 549 (M+H)$^+$; analytical HPLC: t$_{ret}$=2.60 minutes (Grad 1).

Example 91

1-[3-Chloro-4-(4-ethyl-piperazin-1-yl)-phenyl]-3-methyl-8-pyridin-3-yl-1,3-dihydro-imidazo[4,5-c]quinolin-2-one The title compound is obtained in a similar manner as described in Example 1 using 3-chloro-4-(4-ethyl-piperazin-1-yl)-phenylamine (Zerenex, Greater Manchester, UK) and 3-pyridineboronic acid. Title compound: ES-MS: 499 (M+H)$^+$; analytical HPLC: t$_{ret}$=2.24 minutes (Grad 1).

Example 92

1-[3-Chloro-4-(4-ethyl-piperazin-1-yl)-phenyl]-3-methyl-8-quinolin-3-yl-1,3-dihydro-imidazo[4,5-c]quinolin-2-one The title compound is obtained in a similar manner as described in Example 1 using 3-chloro-4-(4-ethyl-piperazin-1-yl)-phenylamine (Zerenex, Greater Manchester, UK) and 3-quinolineboronic acid. Title compound: ES-MS: 549 $(M+H)^+$; analytical HPLC: $t_{ret}$=2.58 minutes (Grad 1).

Example 93

1-[3-Chloro-4-(4-isopropyl-piperazin-1-yl)-phenyl]-3-methyl-8-pyridin-3-yl-1,3-dihydro-imidazo[4,5-c]quinolin-2-one The title compound is obtained in a similar manner as described in Example 1 using 3-chloro-4-(4-isopropyl-piperazin-1-yl)-phenylamine (Example 93a) and 3-pyridineboronic acid. Title compound: ES-MS: 513 $(M+H)^+$; analytical HPLC: $t_{ret}$=2.32 minutes (Grad 1).

Example 93a

3-Chloro-4-(4-isopropyl-piperazin-1-yl)-phenylamine

The title compound is obtained in a similar manner as described in Example 1e using 1-(2-Chloro-4-nitro-phenyl)-4-isopropyl-piperazine (Example 93b). Title compound: ES-MS: 254 $(M+H)^+$; analytical HPLC: $t_{ret}$=1.80 minutes (Grad 1).

Example 93b 1-(2-Chloro-4-nitro-phenyl)-4-isopropyl-piperazine

The title compound is obtained in a similar manner as described in Example 89c using N-isopropylpiperazine (Aldrich, Buchs, Switzerland). Title compound: ES-MS: 284 $(M+H)^+$; analytical HPLC: $t_{ret}$=2.76 minutes (Grad 1).

Example 94

1-[3-Chloro-4-(4-isopropyl-piperazin-1-yl)-phenyl]-3-methyl-8-quinolin-3-yl-1,3-dihydro-imidazo[4,5-c]quinolin-2-one The title compound is obtained in a similar manner as described in Example 1 using 3-chloro-4-(4-isopropyl-piperazin-1-yl)-phenylamine (Example 93a) and 3-quinolineboronic acid. Title compound: ES-MS: 563 $(M+H)^+$; analytical HPLC: $t_{ret}$=2.68 minutes (Grad 1).

Example 95

1-[4-(cis-3,5-Dimethyl-piperazin-1-yl)-3-trifluoromethyl-phenyl]-3-methyl-8-pyridin-3-yl-1,3-dihydro-imidazo[4,5-c]quinolin-2-one The title compound is obtained in a similar manner as described in Example 1 using 4-(4-amino-2-trifluoromethyl-phenyl)-2,6-cis-dimethyl-piperazine-1-carboxylic acid tert-butyl ester (Example 95a) and 3-pyridineboronic acid and removal of the tert-butoxycarbonyl protecting group in a similar manner as described in Example 59. Title compound: ES-MS: 533 $(M+H)^+$; analytical HPLC: $t_{ret}$=2.37 minutes (Grad 1).

Example 95a 4-(4-Amino-2-trifluoromethyl-phenyl)-2,6-cis-dimethyl-piperazine-1-carboxylic acid tert-butyl ester The title compound is obtained in a similar manner as described in Example 1e starting with 4-(4-nitro-2-trifluoromethyl-phenyl)-2,6-cis-dimethyl-piperazine-1-carboxylic acid tert-butyl ester (Example 95b). Title compound: ES-MS: 374 $(M+H)^+$; analytical HPLC: $t_{ret}$=3.79 minutes (Grad 1).

Example 95b cis-2,6-Dimethyl-4-(4-nitro-2-trifluoromethyl-phenyl)-piperazine-1-carboxylic acid tert-butyl ester The title compound is obtained in a similar manner as described in Example 89b starting with cis-3,5-Dimethyl-1-(4-nitro-2-trifluoromethyl-phenyl)-piperazine (Example 89c). Title compound: ES-MS: 404 $(M+H)^+$; analytical HPLC: $t_{ret}$=4.76 minutes (Grad 1).

Example 95c cis-3,5-Dimethyl-1-(4-nitro-2-trifluoromethyl-phenyl)-piperazine

The title compound is obtained in a similar manner as described in Example 18b starting with cis-2,6-dimethylpiperazine (Aldrich, Buchs, Switzerland) and 2-fluoro-5-nitrobenzotrifluoride (Aldrich, Buchs, Switzerland). Title compound: ES-MS: 304 $(M+H)^+$; analytical HPLC: $t_{ret}$=2.89 minutes (Grad 1).

Example 96

1-[4-(cis-3,5-Dimethyl-piperazin-1-yl)-3-trifluoromethyl-phenyl]-3-methyl-8-quinolin-3-yl-1,3-dihydro-imidazo[4,5-c]quinolin-2-one The title compound is obtained in a similar manner as described in Example 1 using 4-(4-amino-2-trifluoromethyl-phenyl)-2,6-cis-dimethyl-piperazine-1-carboxylic acid tert-butyl ester (Example 95a) and 3-quinolineboronic acid and removal of the tert-butoxycarbonyl protecting group in a similar manner as described in Example 59. Title compound: ES-MS: 583 $(M+H)^+$; analytical HPLC: $t_{ret}$=2.71 minutes (Grad 1).

Example 97

1-[4-(4-Ethyl-piperazin-1-yl)-3-trifluoromethyl-phenyl]-3-methyl-8-pyridin-3-yl-1,3-dihydro-imidazo[4,5-c]quinolin-2-one The title compound is obtained in a similar manner as described in Example 1 using 4-(4-ethyl-piperazin-1-yl)-3-trifluoromethyl-phenylamine (Example 97a) and 3-pyridineboronic acid. Title compound: ES-MS: 533 $(M+H)^+$; analytical HPLC: $t_{ret}$=2.38 minutes (Grad 1).

Example 97a 4-(4-Ethyl-piperazin-1-yl)-3-trifluoromethyl-phenylamine

The title compound is obtained in a similar manner as described in Example 95a/c using N-ethylpiperazine (Aldrich, Buchs, Switzerland). Title compound: ES-MS: 274 $(M+H)^+$; analytical HPLC: $t_{ret}$=2.01 minutes (Grad 1).

Example 98

1-[4-(4-Ethyl-piperazin-1-yl)-3-trifluoromethyl-phenyl]-3-methyl-8-quinolin-3-yl-1,3-dihydro-imidazo[4,5-c]quinolin-2-one The title compound is obtained in a similar manner as described in Example 1 using 4-(4-ethyl-piperazin-1-yl)-3-trifluoromethyl-phenylamine (Example 97a) and 3-quinolineboronic acid. Title compound: ES-MS: 583 (M+H)$^+$; analytical HPLC: $t_{ret}$=2.73 minutes (Grad 1).

Example 99

1-[4-(4-Ethyl-piperazin-1-yl)-3-trifluoromethyl-phenyl]-3-methyl-8-pyridin-3-yl-1,3-dihydro-imidazo[4,5-c]quinolin-2-one The title compound is obtained in a similar manner as described in Example 1 using 4-(4-isopropyl-piperazin-1-yl)-3-trifluoromethyl-phenylamine (Example 99a) and 3-pyridineboronic acid. Title compound: ES-MS: 547 (M+H)$^+$; analytical HPLC: $t_{ret}$=2.45 minutes (Grad 1).

Example 99a 4-(4-Isopropyl-piperazin-1-yl)-3-trifluoromethyl-phenylamine

The title compound is obtained in a similar manner as described in Example 95a/c using N-isopropylpiperazine (Aldrich, Buchs, Switzerland). Title compound: ES-MS: 288 (M+H)$^+$; analytical HPLC: $t_{ret}$=2.17 minutes (Grad 1).

Example 100

1-[4-(4-Ethyl-piperazin-1-yl)-3-trifluoromethyl-phenyl]-3-methyl-8-quinolin-3-yl-1,3-dihydro-imidazo[4,5-c]quinolin-2-one The title compound is obtained in a similar manner as described in Example 1 using 4-(4-isopropyl-piperazin-1-yl)-3-trifluoromethyl-phenylamine (Example 99a) and 3-quinolineboronic acid. Title compound: ES-MS: 597 (M+H)$^+$; analytical HPLC: $t_{ret}$=2.82 minutes (Grad 1).

Example 101

3-Methyl-8-(6-piperazin-1-yl-pyridin-3-yl)-1-(3-trifluoromethyl-phenyl)-1,3-dihydro-imidazo[4,5-c]quinolin-2-one The title compound is obtained in a similar manner as described in Example 1 using 2-trifluoromethylaniline (Fluka, Buchs, Switzerland) and 4-[5-(4,4,5,5-Tetramethyl-[1,3,2]dioxaborolan-2-yl)-pyridin-2-yl]-piperazine-1-carboxylic acid tert-butyl ester (CB Research & Development, New Castle, USA) and removal of the tert-butoxycarbonyl protecting group in a similar manner as described in Example 59. Title compound: ES-MS: 505 (M+H)$^+$; analytical HPLC: $t_{ret}$=2.47 minutes (Grad 1).

Example 102

8-(6-Methoxy-pyridin-3-yl)-3-methyl-1-(3-trifluoromethyl-phenyl)-1,3-dihydro-imidazo[4,5-c]quinolin-2-one The title compound is obtained in a similar manner as described in Example 1 using 2-trifluoromethylaniline (Fluka, Buchs, Switzerland) and 2-methoxy-5-pyridineboronic acid (Lancaster, Morecambe, UK). Title compound: ES-MS: 451 (M+H)$^+$; analytical HPLC: $t_{ret}$=3.28 minutes (Grad 1).

Example 103

8-(6-Methoxy-pyridin-3-yl)-3-methyl-1-(3-trifluoromethyl-phenyl)-1,3-dihydro-imidazo[4,5-c]quinolin-2-one The title compound is obtained in a similar manner as described in Example 1 using 2-trifluoromethylaniline (Fluka, Buchs, Switzerland) and 6-benzopyrazineboronic acid hydrochloride (Asychem, Durham, USA). Title compound: ES-MS: 472 (M+H)$^+$; analytical HPLC: $t_{ret}$=3.15 minutes (Grad 1).

Example 104

1-(3-Chloro-4-imidazol-1-yl-phenyl)-3-methyl-8-pyridin-3-yl-1,3-dihydro-imidazo[4,5-c]quinolin-2-one The title compound is obtained in a similar manner as described in Example 1 using 3-chloro-4-imidazol-1-yl-phenylamine (Example 104a) and 3-pyridineboronic acid. Title compound: ES-MS: 453 (M+H)$^+$; analytical HPLC: $t_{ret}$=2.09 minutes (Grad 1).

Example 104a

3-Chloro-4-imidazol-1-yl-phenylamine

The title compound is obtained in a similar manner as described in Example 1e starting with 1-(2-chloro-4-nitrophenyl)-1H-imidazole (Example 104b). Title compound: ES-MS: 194 (M+H)$^+$; analytical HPLC: $t_{ret}$=1.84 minutes (Grad 1).

Example 104b 1-(2-Chloro-4-nitro-phenyl)-1H-imidazole 1.0 g (5.21 mmol) of 3,4-dichloronitrobenzene (Fluka, Buchs, Switzerland), 532 mg (7.81 mmol) imidazole (Aldrich, Buchs, Switzerland) and 1.35 g (10.4 mmol) Hünig's base in 4 ml of DMA are heated in a microwave oven at 180° C. for 1 h 40 min. The reaction mixture is quenched with sat. aqueous NaHCO$_3$ and extracted with EtOAc (2×). The organic layers is washed with sat. aqueous NaHCO$_3$ (3×), with brine, dried over MgSO$_4$, filtered and evaporated. The residue is purified by flash chromatography on silica gel (CH$_2$Cl$_2$-MeOH 1:0 to 93:7) to provide the title compound as an oil. ES-MS: 224 (M+H)$^+$; analytical HPLC: $t_{ret}$=2.11 minutes (Grad 1).

Example 105

1-(3-Chloro-4-imidazol-1-yl-phenyl)-3-methyl-8-quinolin-3-yl-1,3-dihydro-imidazo[4,5-c]quinolin-2-one The title compound is obtained in a similar manner as described in Example 1 using 3-chloro-4-imidazol-1-yl-phenylamine (Example 104a) and 3-quinolineboronic acid. Title compound: ES-MS: 503 (M+H)$^+$; analytical HPLC: $t_{ret}$=2.44 minutes (Grad 1).

Example 106

2-Methyl-2-[4-(3-methyl-8-quinolin-3-yl-2-thioxo-2,3-dihydro-imidazo[4,5-c]quinolin-1-yl)-phenyl]-propionitrile 100 mg (0.213 mmol) of 2-methyl-2-[4-(3-methyl-2-oxo-8-quinolin-3-yl-2,3-dihydro-imidazo[4,5-c]quinolin-1-yl)-phenyl]-propionitrile (Example 7) and 95 mg (0.234 mmol) Lawesson reagent (Fluka, Buchs, Switzerland) in 1 ml of dioxane are heated at 100° C. for 96 h. The reaction mixture is quenched with sat. aqueous NaHCO$_3$ and extracted with CH$_2$Cl$_2$ (2×). The organic layers are washed with sat. aqueous NaHCO$_3$, dried over Na$_2$SO$_4$, filtered and evaporated. The residue is purified by preparative HPLC to provide the title compound as an off-white solid. ES-MS: 486 (M+H)$^+$; analytical HPLC: t$_{ret}$=3.29 minutes (Grad 1).

Example 107

2-Methyl-2-{4-[3-methyl-8-(2-methyl-pyridin-4-yl)-2-oxo-2,3-dihydro-imidazo[4,5-c]quinolin-1-yl]-phenyl}-propionitrile The title compound is obtained in a similar manner as described in Example 1 using 2-methyl-4-pyridylboronic acid (Asymchem, Durham, USA). Title compound: ES-MS: 434 (M+H)$^+$; analytical HPLC: t$_{ret}$=2.44 minutes (Grad 1).

Example 108

5-(1-[4-(Cyano-dimethyl-methyl)-phenyl]-3-methyl-2-oxo-2,3-dihydro-1H-imidazo[4,5-c]quinolin-8-yl)-pyridine-2-carbonitrile The title compound is obtained in a similar manner as described in Example 1 using 2-cyano-5-(4,4,5,5-tetramethyl-1,3,2-dioxaborolan-2-yl)pyridine (Frontier Scientific, Logan, USA). Title compound: ES-MS: 445.5 (M+H)$^+$; analytical HPLC: t$_{ret}$=4.42 minutes (Grad 2).

Example 109

2-[4-(4-Amino-3-methyl-2-oxo-8-quinolin-3-yl-2,3-dihydro-imidazo[4,5-c]quinolin-1-yl)-phenyl]-2-methyl-propionitrile 110 mg (0.182 mmol) of 2-{4-[4-(4-methoxy-benzylamino)-3-methyl-2-oxo-8-quinolin-3-yl)-2,3-dihydro-imidazo[4,5-c]quinolin-1-yl]-phenyl}-2-methyl-propionitrile (Example 109a) in 1.1 ml TFA are stirred at rt for 24 h and then at 35° C. for 5 h. The reaction mixture is purified by preparative HPLC to provide the title compound as an off-white solid. ES-MS: 485 (M+H)$^+$; analytical HPLC: t$_{ret}$=2.86 minutes (Grad 1).

Example 109a

2-{4-[4-(4-Methoxy-benzylamino)-3-methyl-2-oxo-8-quinolin-3-yl-2,3-dihydro-imidazo[4,5-c]quinolin-1-yl]-phenyl}-2-methyl-propionitrile 100 mg (0.198 mmol) of 2-[4-(4-chloro-3-methyl-2-oxo-8-quinolin-3-yl-2,3-dihydro-imidazo[4,5-c]quinolin-1-yl)-phenyl]-2-methyl-propionitrile (Example 109b), 27 mg (0.278 mmol) sodium tert-butanolate, 11 mg (0.02 mmol) SK-CC01-A catalyst and 33 mg (0.238 mmol) 4-methoxy-benzylamine in 0.4 ml degassed toluene under argon are heated at 100° C. for 22 h. The reaction mixture is quenched with sat. aqueous NaHCO$_3$ and extracted with CH$_2$Cl$_2$ (2×). The organic layers are washed with sat. aqueous NaHCO$_3$, dried over Na$_2$SO$_4$, filtered and evaporated to provide the title compound as a crude brown solid. ES-MS: 605 (M+H)$^+$; analytical HPLC: t$_{ret}$=3.29 minutes (Grad 1).

Example 109b

2-[4-(4-Chloro-3-methyl-2-oxo-8-quinolin-3-yl-2,3-dihydro-imidazo[4,5-c]quinolin-1-yl)-phenyl]-2-methyl-propionitrile 1 g (2.06 mmol) of 2-methyl-2-[4-(3-methyl-2-oxo-5-oxy-8-quinolin-3-yl-2,3-imidazo[4,5-c]quinolin-1-yl)-phenyl]-propionitrile (Example 109c) and 948 mg (6.18 mmol) POCl$_3$ in 25 ml of toluene are heated at 100° C. for 5 h. Are added 948 mg (6.18 mmol) POCl$_3$ and the reaction mixture is heated at 100° C. for 15.5 h. The reaction mixture is quenched with sat. aqueous NaHCO$_3$ and extracted with CH$_2$Cl$_2$ (2×). The organic layers is washed with sat. aqueous NaHCO$_3$, brine, dried over Na$_2$SO$_4$, filtered and evaporated to provide the crude title compound. ES-MS: 504 (M+H)$^+$; analytical HPLC: t$_{ret}$=3.56 minutes (Grad 1).

Example 109c

2-Methyl-2-[4-(3-methyl-2-oxo-5-oxy-8-quinolin-3-yl-2,3-dihydro-imidazo[4,5-c]quinolin-1-yl)-phenyl]-propionitrile The title compound is obtained in a similar manner as described in Example 1 using 2-[4-(8-bromo-3-methyl-2-oxo-5-oxy-2,3-dihydro-imidazo[4,5-c]quinolin-1-yl)-phenyl]-2-methyl-propionitrile (Example 109d) and 3-quinolineboronic acid. Title compound: ES-MS: 486 (M+H)$^+$; analytical HPLC: t$_{ret}$=3.14 minutes (Grad 1).

Example 109d

2-[4-(8-Bromo-3-methyl-2-oxo-5-oxy-2,3-dihydro-imidazo[4,5-c]-quinolin-1-yl)-phenyl]-2-methyl-propionitrile 2 g (4.75 mmol) of 2-[4-(8-bromo-3-methyl-2-oxo-2,3-dihydro-imidazo[4,5-c]quinolin-1-yl)-phenyl]-2-methyl-propionitrile (Example 1i) and 1.58 g (5.22 mmol) 3-chloroperbenzoic acid in 90 ml of CH$_2$Cl$_2$ are stirred at rt for 2 h. The reaction mixture is washed with 10% aqueous Na$_2$CO$_3$ and brine, dried over Na$_2$SO$_4$, filtered and evaporated. The solid is triturated in ethyl acetate to provide the crude title compound. ES-MS: 337, 339 (M+H)$^+$, Br pattern; analytical HPLC: t$_{ret}$=3.47 minutes (Grad 1).

Example 110

1-[4-(3-Methyl-2-oxo-8-pyridin-3-yl-2,3-dihydro-imidazo[4,5-c]quinolin-1-yl)-phenyl]-cyclopropanecarbonitrile The title compound is obtained in a similar manner as described in Example 1 using 1-(4-amino-phenyl)-cyclopropanecarbonitrile (Example 110a) and 3-pyridineboronic acid. Title compound: ES-MS: 418 (M+H)$^+$; analytical HPLC: t$_{ret}$=3.82 minutes (Grad 2).

Example 110a 1-(4-Amino-phenyl)-cyclopropanecarbonitrile 750 mg (4 mmol) of 4-(1-cyano-cyclopropyl)-benzoic acid (Example 110b) in 20 ml of tert-butanol are stirred in presence of 0.86 ml (4 mmol) diphenylphosphoryl azide (DPPA, Fluka, Buchs, Switzerland) and 0.59 ml (4 mmol) triethylamine at 95° C. for 3 h. Are added 0.43 ml (2 mmol) DPPA and 0.29 ml (2 mmol) triethylamine and the reaction mixture is stirred at 95° C. for 30 min. The reaction mixture is evaporated to dryness and then is taken in EtOAc and washed with H$_2$O, dried over Na$_2$SO$_4$, filtered and evaporated. The solid is separated by flash chromatography (CH$_2$Cl$_2$-MeOH 99:1). The purified compound is treated in 5 ml 4 M HCl in dioxane at rt for 2 h. The crude deprotected product is purified by flash chromatography (CH$_2$Cl$_2$-MeOH 98:2). The product is triturated in MeOH to give the title compound. Analytical HPLC: t$_{ret}$=3.68 minutes (Grad 2).

Example 110b

4-(1-Cyano-cyclopropyl)-benzoic acid

To 2 g (12.4 mmol) of 4-(cyanomethyl)benzoic acid (Ubichem, Eastleigh, UK) and 10.9 ml (124 mmol) 1,2-dibromoethane (Fluka, Buchs, Switzerland) cooled at 0° C. with an ice-bath are added a solution of 14.4 g (62 mmol) benzyltriethylammonium chloride in 50 ml 8 M aqueous NaOH. The reaction mixture is stirred over night at rt and then is acidified at pH 1-2 with 6 M aqueous HCl and is extracted with EtOAc. The organic layer is washed with $H_2O$ (2×) and evaporated to dryness. The solid is triturated in MeOH to provide the crude title compound. ES-MS: 186 (M–H)$^-$; analytical HPLC: $t_{ret}$=4.43 minutes (Grad 2).

Example 111

1-[4-(3-Methyl-2-oxo-8-quinolin-3-yl-2,3-dihydro-imidazo[4,5-c]quinolin-1-yl)-phenyl]-cyclopropanecarbonitrile The title compound is obtained in a similar manner as described in Example 1 using 1-(4-amino-phenyl)-cyclopropanecarbonitrile (Example 110a) and 3-quinolineboronic acid. Title compound: ES-MS: 468 (M+H)$^+$; analytical HPLC: $t_{ret}$=4.14 minutes (Grad 2).

Example 112

1-{4-[8-(6-Methoxy-pyridin-3-yl)-3-methyl-2-oxo-2,3-dihydro-imidazo[4,5-c]quinolin-1-yl]-phenyl}-cyclopropanecarbonitrile The title compound is obtained in a similar manner as described in Example 1 using 1-(4-amino-phenyl)-cyclopropanecarbonitrile (Example 110a) and 2-methoxy-5-pyridineboronic acid. Title compound: ES-MS: 448.5 (M+H)$^+$; analytical HPLC: $t_{ret}$=4.42 minutes (Grad 2).

Example 113

1-[3-Chloro-4-(4-methyl-piperazin-1-yl)-phenyl]-8-(6-methoxy-pyridin-3-yl)-3-methyl-1,3-dihydro-imidazo[4,5-c]quinolin-2-one The title compound is obtained as described in Example 65 using 2-methoxy-5-pyridineboronic acid. Title compound: ES-MS: 515 (M+H)$^+$; analytical HPLC: $t_{ret}$=3.83 minutes (Grad 2).

Example 114

1-[3-Chloro-4-(4-methyl-piperazin-1-yl)-phenyl]-8-(5-methoxy-pyridin-3-yl)-3-methyl-1,3-dihydro-imidazo[4,5-c]quinolin-2-one The title compound is obtained as described in Example 65 using 3-methoxy-5-(4,4,5,5-tetramethyl-1,3,2-dioxaborolan-2-yl)pyridine. Title compound: ES-MS: 515.5 (M+H)$^+$; analytical HPLC: $t_{ret}$=3.60 minutes (Grad 2).

Example 115

1-[3-Chloro-4-(4-methyl-piperazin-1-yl)-phenyl]-3-methyl-8-quinoxalin-6-yl-1,3-dihydro-imidazo[4,5-c]quinolin-2-one The title compound is obtained as described in Example 65 using 6-benzopyrazineboronic acid hydrochloride. Title compound: ES-MS: 536.6 (M+H)$^+$; analytical HPLC: $t_{ret}$=3.80 minutes (Grad 2).

Example 116

1-(3-Chloro-4-piperazin-1-yl-phenyl)-8-(2-methoxy-pyrimidin-5-yl)-3-methyl-1,3-dihydro-imidazo[4,5-c]quinolin-2-one The title compound is obtained as described in Example 75 using 2-methoxy-5-pyrimidineboronic acid (Frontier Scientific, Logan, USA). Title compound: ES-MS: 502 (M+H)$^+$; analytical HPLC: $t_{ret}$=2.40 minutes (Grad 1).

Example 117

1-(3-Chloro-4-piperazin-1-yl-phenyl)-3-methyl-8-pyrimidin-5-yl-1,3-dihydro-imidazo[4,5-c]quinolin-2-one The title compound is obtained as described in Example 75 using 5-pyrimidineboronic acid (Frontier Scientific, Logan, USA). Title compound: ES-MS: 472 (M+H)$^+$; analytical HPLC: $t_{ret}$=2.26 minutes (Grad 1).

Example 118

1-(3-Chloro-4-piperazin-1-yl-phenyl)-3-methyl-8-(2-methyl-pyridin-4-yl)-1,3-dihydro-imidazo[4,5-c]quinolin-2-one The title compound is obtained as described in Example 75 using 2-picoline-4-boronic acid. Title compound: ES-MS: 485 (M+H)$^+$; analytical HPLC: $t_{ret}$=2.14 minutes (Grad 1).

Example 119

1-[3-Chloro-4-(cis-3,5-dimethyl-piperazin-1-yl)-phenyl]-8-(6-methoxy-pyridin-3-yl)-3-methyl-1,3-dihydro-imidazo[4,5-c]quinolin-2-one The title compound is obtained in a similar manner as described in Example 89 using 2-methoxy-5-pyridineboronic acid and removal of the tert-butoxycarbonyl protecting group in a similar manner as described in Example 59. Title compound: ES-MS: 529 (M+H)$^+$; analytical HPLC: $t_{ret}$=2.66 minutes (Grad 1).

Example 120

1-[3-Chloro-4-(cis-3,5-dimethyl-piperazin-1-yl)-phenyl]-8-(5-methoxy-pyridin-3-yl)-3-methyl-1,3-dihydro-imidazo[4,5-c]quinolin-2-one The title compound is obtained in a similar manner as described in Example 89 using 3-methoxy-5-(4,4,5,5-tetramethyl-1,3,2-dioxaborolan-2-yl)pyridine and removal of the tert-butoxycarbonyl protecting group in a similar manner as described in Example 59. Title compound: ES-MS: 529 (M+H)$^+$; analytical HPLC: $t_{ret}$=2.40 minutes (Grad 1).

Example 121

1-[4-(cis-3,5-Dimethyl-piperazin-1-yl)-3-trifluoromethyl-phenyl]-8-(6-methoxy-pyridin-3-yl)-3-methyl-1,3-dihydro-imidazo[4,5-c]quinolin-2-one The title compound is obtained in a similar manner as described in Example 1 using 4-(4-amino-2-trifluoromethyl-phenyl)-2,6-cis-dimethyl-piperazine-1-carboxylic acid tert-butyl ester (Example 95a) and 2-methoxy-5-pyridineboronic acid and removal of the tert-butoxycarbonyl protecting group in a similar manner as described in Example 59. Title compound: ES-MS: 563 (M+H)$^+$; analytical HPLC: $t_{ret}$=2.76 minutes (Grad 1).

Example 122

1-[4-(cis-3,5-Dimethyl-piperazin-1-yl)-3-trifluoromethyl-phenyl]-8-(5-methoxy-pyridin-3-yl)-3-methyl-1,3-dihydro-imidazo[4,5-c]quinolin-2-one The title compound is obtained in a similar manner as described in Example 1 using 4-(4-amino-2-trifluoromethyl-phenyl)-2,6-cis-dimethyl-piperazine-1-carboxylic acid tert-butyl ester (Example 95a) and 3-methoxy-5-(4,4,5,5-tetramethyl-1,3,2-dioxaborolan-2-yl)pyridine and removal of the tert-butoxycarbonyl protecting group in a similar manner as described in Example 59. Title compound: ES-MS: 563 (M+H)$^+$; analytical HPLC: $t_{ret}$=2.50 minutes (Grad 1).

Example 123

8-(2-Methoxy-pyrimidin-5-yl)-3-methyl-1-(4-piperazin-1-yl-3-trifluoromethyl-phenyl)-1,3-dihydro-imidazo[4,5-c]quinolin-2-one The title compound is obtained as described in Example 84 using 2-methoxy-5-pyridineboronic acid. Title compound: ES-MS: 536.5 (M+H)$^+$; analytical HPLC: $t_{ret}$=3.78 minutes (Grad 2).

Example 124

3-Methyl-1-(4-piperazin-1-yl-3-trifluoromethyl-phenyl)-8-pyrimidin-5-yl-1,3-dihydro-imidazo[4,5-c]quinolin-2-one The title compound is obtained as described in Example 84 using 5-pyrimidineboronic acid. Title compound: ES-MS: 506 (M+H)$^+$; analytical HPLC: $t_{ret}$=3.66 minutes (Grad 2).

Example 125

5-[3-Methyl-2-oxo-1-(4-piperazin-1-yl-3-trifluoromethyl-phenyl)-2,3-dihydro-1H-imidazo[4,5-c]quinolin-8-yl]-pyridine-2-carbonitrile The title compound is obtained as described in Example 84 using 2-cyano-5-(4,4,5,5-tetramethyl-1,3,2-dioxaborolan-2-yl)pyridine. Title compound: ES-MS: 530.6 (M+H)$^+$; analytical HPLC: $t_{ret}$=3.89 minutes (Grad 2).

Example 126

3-Methyl-8-(2-methyl-pyridin-4-yl)-1-(4-piperazin-1-yl-3-trifluoromethyl-phenyl)-1,3-dihydro-imidazo[4,5-c]quinolin-2-one The title compound is obtained as described in Example 84 using 2-methyl-4-pyridylboronic acid. Title compound: ES-MS: 519 (M+H)$^+$; analytical HPLC: $t_{ret}$=3.63 minutes (Grad 2).

Example 127

8-(3,4-Dimethoxy-phenyl)-3-methyl-1-(4-piperazin-1-yl-3-trifluoromethyl-phenyl)-1,3-dihydro-imidazo[4,5-c]quinolin-2-one The title compound is obtained as described in Example 84 using 3,4-dimethoxyphenylboronic acid (Aldrich, Buchs, Switzerland). Title compound: ES-MS: 564 (M+H)$^+$; analytical HPLC: $t_{ret}$=2.68 minutes (Grad 1).

Example 128

3-Methyl-8-pyridin-3-yl-1-(4-[1,2,4]triazol-1-yl-3-trifluoromethyl-phenyl)-1,3-dihydro-imidazo[4,5-c]quinolin-2-one The title compound is obtained as described in Example 1 using 4-[1,2,4]triazol-1-yl-3-trifluoromethylphenylamine (Example 128a). Title compound: ES-MS: 488 (M+H)$^+$; analytical HPLC: $t_{ret}$=3.72 minutes (Grad 2).

Example 128a

4-[1,2,4]Triazol-1-yl-3-trifluoromethyl-phenylamine

The title compound is obtained in a similar manner as Example 71a using 1-fluoro-4-nitro-2-trifluoromethyl-benzene (Aldrich, Buchs, Switzerland) and 1,2,4-triazole (Fluka, Buchs, Switzerland). Title compound: ES-MS: 229 (M+H)$^+$; analytical HPLC: $t_{ret}$=4.14 minutes (Grad 2).

Example 129

3-Methyl-8-quinolin-3-yl-1-(4-[1,2,4]triazol-1-yl-3-trifluoromethyl-phenyl)-1,3-dihydro-imidazo[4,5-c]quinolin-2-one The title compound is obtained as described in Example 128 using 3-quinolineboronic acid. Title compound: ES-MS: 538 (M+H)$^+$; analytical HPLC: $t_{ret}$=4.03 minutes (Grad 2).

Example 130

8-(6-Methoxy-pyridin-3-yl)-3-methyl-1-(4-[1,2,4]triazol-1-yl-3-trifluoromethyl-phenyl)-1,3-dihydro-imidazo[4,5-c]quinolin-2-one The title compound is obtained as described in Example 128 using 2-methoxy-5-pyridineboronic acid. Title compound: ES-MS: 518 (M+H)$^+$; analytical HPLC: $t_{ret}$=4.25 minutes (Grad 2).

Example 131

8-(5-Methoxy-pyridin-3-yl)-3-methyl-1-(4-[1,2,4]triazol-1-yl-3-trifluoromethyl-phenyl)-1,3-dihydro-imidazo[4,5-c]quinolin-2-one The title compound is obtained as described in Example 128 using 3-methoxy-5-(4,4,5,5-tetramethyl-1,3,2-dioxaborolan-2-yl)pyridine. Title compound: ES-MS: 518 (M+H)$^+$; analytical HPLC: $t_{ret}$=3.85 minutes (Grad 2).

Example 132

5-[3-Methyl-2-oxo-1-(4-[1,2,4]triazol-1-yl-3-trifluoromethyl-phenyl)-2,3-dihydro-1H-imidazo[4,5-c]quinolin-8-yl]-pyridine-2-carbonitrile The title compound is obtained as described in Example 128 using 2-cyano-5-(4,4,5,5-tetramethyl-1,3,2-dioxaborolan-2-yl)pyridine. Title compound: ES-MS: 513.6 (M+H)$^+$; analytical HPLC: $t_{ret}$=4.21 minutes (Grad 2).

Example 133

8-(6-Fluoro-pyridin-3-yl)-3-methyl-1-(4-[1,2,4]triazol-1-yl-3-trifluoromethyl-phenyl)-1,3-dihydro-imidazo[4,5-c]quinolin-2-one The title compound is obtained as described in Example 128 using 2-fluoro-5-pyridineboronic acid (Frontier Scientific, Logan, USA). Title compound: ES-MS: 506 (M+H)$^+$; analytical HPLC: $t_{ret}$=4.19 minutes (Grad 2).

Example 134

8-(2,6-Dimethoxy-pyridin-3-yl)-3-methyl-1-(4-[1,2,4]triazol-1-yl-3-trifluoromethyl-phenyl)-1,3-dihydro-imidazo[4,5-c]quinolin-2-one The title compound is obtained as described in Example 128 using 2,6-dimethoxy-3-pyridineboronic acid (Lancaster, Morecambe, UK). Title compound: ES-MS: 548.6 (M+H)$^+$; analytical HPLC: $t_{ret}$=4.54 minutes (Grad 2).

Example 135

3-Methyl-8-pyrimidin-5-yl-1-(4-[1,2,4]triazol-1-yl-3-trifluoromethyl-phenyl)-1,3-dihydro-imidazo[4,5-c]quinolin-2-one The title compound is obtained as described in Example 128 using 5-pyrimidineboronic acid. Title compound: ES-MS: 489.6 (M+H)$^+$; analytical HPLC: $t_{ret}$=3.93 minutes (Grad 2).

Example 136

8-(2-Methoxy-pyrimidin-5-yl)-3-methyl-1-(4-[1,2,4]triazol-1-yl-3-trifluoromethyl-phenyl)-1,3-dihydro-imidazo[4,5-c]quinolin-2-one The title compound is obtained as described in Example 128 using 2-methoxy-5-pyridineboronic acid. Title compound: ES-MS: 519 (M+H)$^+$; analytical HPLC: $t_{ret}$=4.12 minutes (Grad 2).

Example 137

8-(2,4-Dimethoxy-pyrimidin-5-yl)-3-methyl-1-(4-[1,2,4]triazol-1-yl-3-trifluoromethyl-phenyl)-1,3-dihydro-imidazo[4,5-c]quinolin-2-one The title compound is obtained as described in Example 128 using 2,4-dimethoxy-5-pyridineboronic acid (Frontier Scientific, Logan, USA). Title compound: ES-MS: 549 (M+H)$^+$; analytical HPLC: $t_{ret}$=4.19 minutes (Grad 2).

Example 138

3-Methyl-1-(4-pyrazol-1-yl-3-trifluoromethyl-phenyl)-8-pyridin-3-yl-1,3-dihydro-imidazo[4,5-c]quinolin-2-one The title compound is obtained as described in Example 1 using 4-pyrazol-1-yl-3-trifluoromethyl-phenylamine (Example 137a). Title compound: ES-MS: 487 (M+H)$^+$; analytical HPLC: $t_{ret}$=3.92 minutes (Grad 2).

Example 138a

4-Pyrazol-1-yl-3-trifluoromethyl-phenylamine

The title compound is obtained in a similar manner as Example 71a using 1-fluoro-4-nitro-2-trifluoromethyl-benzene (Aldrich, Buchs, Switzerland) and pyrazole (Fluka, Buchs, Switzerland). Title compound: ES-MS: 228 (M+H)$^+$; analytical HPLC: $t_{ret}$=4.58 minutes (Grad 2).

Example 139

3-Methyl-1-(4-pyrazol-1-yl-3-trifluoromethyl-phenyl)-8-quinolin-3-yl-1,3-dihydro-imidazo[4,5-c]quinolin-2-one The title compound is obtained as described in Example 138 using 3-quinolineboronic acid. Title compound: ES-MS: 537 (M+H)$^+$; analytical HPLC: $t_{ret}$=4.29 minutes (Grad 2).

Example 140

8-(6-Methoxy-pyridin-3-yl)-3-methyl-1-(4-pyrazol-1-yl-3-trifluoromethyl-phenyl)-1,3-dihydro-imidazo[4,5-c]quinolin-2-one The title compound is obtained as described in Example 138 using 2-methoxy-5-pyridineboronic acid. Title compound: ES-MS: 517 (M+H)$^+$; analytical HPLC: $t_{ret}$=4.57 minutes (Grad 2).

Example 141

8-(5-Methoxy-pyridin-3-yl)-3-methyl-1-(4-pyrazol-1-yl-3-trifluoromethyl-phenyl)-1,3-dihydro-imidazo[4,5-c]quinolin-2-one The title compound is obtained as described in Example 138 using 3-methoxy-5-(4,4,5,5-tetramethyl-1,3,2-dioxaborolan-2-yl)pyridine. Title compound: ES-MS: 517 (M+H)$^+$; analytical HPLC: $t_{ret}$=4.07 minutes (Grad 2).

Example 142

1-(3-Chloro-4-[1,2,4]triazol-1-yl-phenyl)-3-methyl-8-pyridin-3-yl-1,3-dihydro-imidazo[4,5-c]quinolin-2-one The title compound is obtained in a similar manner as described in Example 1 starting with 3-chloro-4-[1,2,4]triazol-1-yl-phenylamine (Example 142a). Title compound: ES-MS: 454 (M+H)$^+$; analytical HPLC: $t_{ret}$=2.28 minutes (Grad 1).

Example 142a

3-Chloro-4-[1,2,4]triazol-1-yl-phenylamine

The title compound is obtained in a similar manner as described in Example 104a/b starting with 1,2,4-triazole. Title compound: ES-MS: 195 (M+H)$^+$; analytical HPLC: $t_{ret}$=2.09 minutes (Grad 1).

Example 143

1-(3-Chloro-4-[1,2,4]triazol-1-yl-phenyl)-3-methyl-8-quinolin-3-yl-1,3-dihydro-imidazo[4,5-c]quinolin-2-one The title compound is obtained in a similar manner as described in Example 142 starting with 3-quinolineboronic acid. Title compound: ES-MS: 504 (M+H)$^+$; analytical HPLC: $t_{ret}$=2.67 minutes (Grad 1).

Example 144

1-(4-Imidazol-1-yl-3-trifluoromethyl-phenyl)-3-methyl-8-pyridin-3-yl-1,3-dihydro-imidazo[4,5-c]quinolin-2-one The title compound is obtained as described in Example 1 using 4-pyrazol-1-yl-3-trifluoromethyl-phenylamine (Example 144a). Title compound: ES-MS: 487 (M+H)$^+$; analytical HPLC: $t_{ret}$=3.54 minutes (Grad 2).

Example 144a

4-Imidazol-1-yl-3-trifluoromethyl-phenylamine

The title compound is obtained in a similar manner as Example 138a using imidazole. Title compound: ES-MS: 228 (M+H)$^+$; analytical HPLC: $t_{ret}$=3.73 minutes (Grad 2).

Example 145

1-(4-Imidazol-1-yl-3-trifluoromethyl-phenyl)-3-methyl-8-quinolin-3-yl-1,3-dihydro-imidazo[4,5-c]quinolin-2-one The title compound is obtained as described in Example 144 using 3-quinolineboronic acid. Title compound: ES-MS: 537 (M+H)$^+$; analytical HPLC: $t_{ret}$=3.83 minutes (Grad 2).

Example 146

1-(4-Imidazol-1-yl-3-trifluoromethyl-phenyl)-8-(6-methoxy-pyridin-3-yl)-3-methyl-1,3-dihydro-imidazo[4,5-c]quinolin-2-one The title compound is obtained as described in Example 144 using 2-methoxy-5-pyridineboronic acid. Title compound: ES-MS: 517 (M+H)$^+$; analytical HPLC: $t_{ret}$=3.90 minutes (Grad 2).

Example 147

1-(4-Imidazol-1-yl-3-trifluoromethyl-phenyl)-8-(5-methoxy-pyridin-3-yl)-3-methyl-1,3-dihydro-imidazo[4,5-c]quinolin-2-one The title compound is obtained as described in Example 144 using 3-methoxy-5-(4,4,5,5-tetramethyl-1,3,2-dioxaborolan-2-yl)pyridine. Title compound: ES-MS: 517 (M+H)$^+$; analytical HPLC: $t_{ret}$=3.64 minutes (Grad 2).

Example 148

3-Methyl-8-pyridin-3-yl-1-(4-[1,2,4]triazol-1-ylmethyl-phenyl)-1,3-dihydro-imidazo[4,5-c]quinolin-2-one The title compound is obtained in a similar manner as described in Example 1 starting with 4-[1,2,4]Triazol-1-ylmethyl-phenylamine (Example 148a). Title compound: ES-MS: 434 (M+H)$^+$; analytical HPLC: $t_{ret}$=2.13 minutes (Grad 1).

Example 148a

4-[1,2,4]Triazol-1-ylmethyl-phenylamine

The title compound is obtained in a similar manner as described in Example 1e starting with 1-(4-nitro-benzyl)-1H-[1,2,4]triazole (Example 148b). Title compound: ES-MS: 175 (M+H)$^+$; analytical HPLC: $t_{ret}$=minutes (Grad 2).

Example 148b 1-(4-Nitro-benzyl)-1H-[1,2,4]triazole 1.0 g (4.63 mmol) of 4-nitrobenzyl bromide (Fluka, Buchs, Switzerland), 799 mg (11.6 mmol) of 1,2,4-triazole and 0.692 mL (4.63 mmol) of 1,5-diazabicyclo[5.4.0]-5-undecene (Fluka, Buchs, Switzerland) in 10 ml of CH$_2$Cl$_2$ are stirred at rt for 1.5 h. The reaction mixture is quenched with sat. aqueous NaHCO$_3$ and extracted with CH$_2$Cl$_2$ (2×). The organic layers are washed with brine, dried over MgSO$_4$, filtered and evaporated. The residue is purified by flash chromatography (CH$_2$Cl$_2$-MeOH 49:1 to 19:1) to provide the title compound as a pale yellow solid. ES-MS: 205 (M+H)$^+$; analytical HPLC: $t_{ret}$=2.54 minutes (Grad 1).

Example 149

3-Methyl-8-quinolin-3-yl-1-(4-[1,2,4]triazol-1-ylmethyl-phenyl)-1,3-dihydro-imidazo[4,4-c]quinolin-2-one The title compound is obtained as described in Example 148 using 3-quinolineboronic acid. Title compound: ES-MS: 484 (M+H)$^+$; analytical HPLC: $t_{ret}$=2.49 minutes (Grad 1).

Example 150

1-(4-Imidazol-1-ylmethyl-phenyl)-3-methyl-8-pyridin-3-yl-1,3-dihydro-imidazo[4,5-c]quinolin-2-one The title compound is obtained in a similar manner as described in Example 1 starting with 4-imidazol-1-ylmethyl-phenylamine (Example 150a). Title compound: ES-MS: 433 (M+H)$^+$; analytical HPLC: $t_{ret}$=1.96 minutes (Grad 1).

Example 150a

4-Imidazol-1-ylmethyl-phenylamine

The title compound is obtained in a similar manner as described in Example 147a/b starting with imidazole. Title compound: ES-MS: 174 (M+H)$^+$; analytical HPLC: $t_{ret}$=minutes (Grad 2).

Example 151

1-(4-Imidazol-1-ylmethyl-phenyl)-3-methyl-8-quinolin-3-yl-1,3-dihydro-imidazo[4,5-c]quinolin-2-one The title compound is obtained as described in Example 150 using 3-quinolineboronic acid. Title compound: ES-MS: 483 (M+H)$^+$; analytical HPLC: $t_{ret}$=2.33 minutes (Grad 1).

Example 152

The following 4-toluenesulfonic acid salts are prepared in a stoichiometric ratio of 1:1 following standard reaction conditions in analogy to or according to methods that are known in the art:

152-1) 4-Toluenesulfonic acid 2-methyl-2-[4-(3-methyl-2-oxo-8-pyridin-4-yl-2,3-dihydro-imidazo[4,5-c]quinolin-1-yl)-phenyl]-propionitrile salt;
152-2) 4-Toluenesulfonic acid 2-methyl-2-[4-(3-methyl-2-oxo-8-pyridin-3-yl-2,3-dihydro-imidazo[4,5-c]quinolin-1-yl)-phenyl]-propionitrile salt;
152-3) 4-Toluenesulfonic acid 2-methyl-2-[4-(3-methyl-2-oxo-8-quinolin-3-yl-2,3-dihydro-imidazo[4,5-c]quinolin-1-yl)-phenyl]-propionitrile salt;
152-4) 4-Toluenesulfonic acid 2-methyl-2-[4-(3-methyl-2-oxo-8-quinolin-6-yl-2,3-dihydro-imidazo[4,5-c]quinolin-1-yl)-phenyl]-propionitrile salt;
152-5) 4-Toluenesulfonic acid 2-methyl-2-[4-(3-methyl-2-oxo-8-quinoxalin-6-yl-2,3-dihydro-imidazo[4,5-c]quinolin-1-yl)-phenyl]-propionitrile salt;

152-6) 4-Toluenesulfonic acid 2-ethyl-2-[4-(3-methyl-2-oxo-8-pyridin-3-yl-2,3-dihydro-imidazo[4,5-c]quinolin-1-yl)-phenyl]-butyronitrile salt;

152-7) 4-Toluenesulfonic acid 2-ethyl-2-[4-(3-methyl-2-oxo-8-quinolin-3-yl-2,3-dihydro-imidazo[4,5-c]quinolin-1-yl)-phenyl]-butyronitrile salt;

152-8) 4-Toluenesulfonic acid 1-[3-fluoro-4-(2-oxo-pyrrolidin-1-yl)-phenyl]-3-methyl-8-pyridin-3-yl-1,3-dihydro-imidazo[4,5-c]quinolin-2-one salt;

152-9) 4-Toluenesulfonic acid 1-[3-fluoro-4-(2-oxo-pyrrolidin-1-yl)-phenyl]-3-methyl-8-quinolin-3-yl-1,3-dihydro-imidazo[4,5-c]quinolin-2-one salt;

152-10) 4-Toluenesulfonic acid 3-methyl-1-[4-(2-oxo-pyrrolidin-1-yl)-phenyl]-8-pyridin-3-yl-1,3-dihydro-imidazo[4,5-c]quinolin-2-one salt;

152-11) 4-Toluenesulfonic acid 3-methyl-1-[4-(2-oxo-pyrrolidin-1-yl)-phenyl]-8-quinolin-3-yl-1,3-dihydro-imidazo[4,5-c]quinolin-2-one salt;

152-12) 4-Toluenesulfonic acid 1-{4-[bis-(2-methoxy-ethyl)-amino]-3-fluoro-phenyl}-3-methyl-8-pyridin-3-yl-1,3-dihydro-imidazo[4,5-c]quinolin-2-one salt;

152-13) 4-Toluenesulfonic acid 1-{4-[bis-(2-methoxy-ethyl)-amino]-3-fluoro-phenyl}-3-methyl-8-quinolin-3-yl-1,3-dihydro-imidazo[4,5-c]quinolin-2-one salt;

152-14) 4-Toluenesulfonic acid 1-{4-[bis-(2-methoxy-ethyl)-amino]-phenyl}-3-methyl-8-pyridin-3-yl-1,3-dihydro-imidazo[4,5-c]quinolin-2-one salt;

152-15) 4-Toluenesulfonic acid 1-{4-[bis-(2-methoxy-ethyl)-amino]-phenyl}-3-methyl-8-quinolin-3-yl-1,3-dihydro-imidazo[4,5-c]quinolin-2-one salt;

152-16) 4-Toluenesulfonic acid 3-methyl-1-naphthalen-2-yl-8-pyridin-3-yl-1,3-dihydro-imidazo[4,5-c]quinolin-2-one salt;

152-17) 4-Toluenesulfonic acid 3-methyl-1-naphthalen-2-yl-8-quinolin-3-yl-1,3-dihydro-imidazo[4,5-c]quinolin-2-one salt;

152-18) 4-Toluenesulfonic acid 1-(2-chloro-phenyl)-3-methyl-8-pyridin-3-yl-1,3-dihydro-imidazo[4,5-c]quinolin-2-one salt;

152-19) 4-Toluenesulfonic acid 1-(2-chloro-phenyl)-3-methyl-8-quinolin-3-yl-1,3-dihydro-imidazo[4,5-c]quinolin-2-one salt;

152-20) 4-Toluenesulfonic acid 3-methyl-8-pyridin-3-yl-1-o-tolyl-1,3-dihydro-imidazo[4,5-c]quinolin-2-one salt;

152-21) 4-Toluenesulfonic acid 3-methyl-8-quinolin-3-yl-1-o-tolyl-1,3-dihydro-imidazo[4,5-c]quinolin-2-one salt;

152-22) 4-Toluenesulfonic acid 1-(2-ethyl-phenyl)-3-methyl-8-pyridin-3-yl-1,3-dihydro-imidazo[4,5-c]quinolin-2-one salt;

152-23) 4-Toluenesulfonic acid 1-(2-ethyl-phenyl)-3-methyl-8-quinolin-3-yl-1,3-dihydro-imidazo[4,5-c]quinolin-2-one salt;

152-24) 4-Toluenesulfonic acid 3-methyl-8-pyridin-3-yl-1-(2-trifluoromethyl-phenyl)-1,3-dihydro-imidazo[4,5-c]quinolin-2-one salt;

152-25) 4-Toluenesulfonic acid 3-methyl-8-quinolin-3-yl-1-(2-trifluoromethyl-phenyl)-1,3-dihydro-imidazo[4,5-c]quinolin-2-one salt;

152-26) 4-Toluenesulfonic acid 1-(4-fluoro-2-methyl-phenyl)-3-methyl-8-quinolin-3-yl-1,3-dihydro-imidazo[4,5-c]quinolin-2-one salt;

152-27) 4-Toluenesulfonic acid 1-(4-fluoro-2-methyl-phenyl)-3-methyl-8-quinolin-3-yl-1,3-dihydro-imidazo[4,5-c]quinolin-2-one salt;

152-28) 4-Toluenesulfonic acid 1-(2-chloro-4-fluoro-phenyl)-3-methyl-8-pyridin-3-yl-1,3-dihydro-imidazo[4,5-c]quinolin-2-one salt;

152-29) 4-Toluenesulfonic acid 1-(2-chloro-4-fluoro-phenyl)-3-methyl-8-quinolin-3-yl-1,3-dihydro-imidazo[4,5-c]quinolin-2-one salt;

152-30) 4-Toluenesulfonic acid 1-(3-chloro-phenyl)-3-methyl-8-pyridin-3-yl-1,3-dihydro-imidazo[4,5-c]quinolin-2-one salt;

152-31) 4-Toluenesulfonic acid 1-(3-chloro-phenyl)-3-methyl-8-quinolin-3-yl-1,3-dihydro-imidazo[4,5-c]quinolin-2-one salt;

152-32) 4-Toluenesulfonic acid 1-(4-methoxymethyl-phenyl)-3-methyl-8-quinolin-3-yl-1,3-dihydro-imidazo[4,5-c]quinolin-2-one salt;

152-33) 4-Toluenesulfonic acid 1-[2-chloro-4-(2-methoxy-ethyl)-phenyl]-3-methyl-8-quinolin-3-yl-1,3-dihydro-imidazo[4,5-c]quinolin-2-one salt;

152-34) 4-Toluenesulfonic acid 1-[4-(2-methoxy-ethyl)-phenyl]-3-methyl-8-pyridin-3-yl-1,3-dihydro-imidazo[4,5-c]quinolin-2-one salt;

152-35) 4-Toluenesulfonic acid 2-methyl-2-[4-(3-methyl-2-oxo-5-oxy-8-pyridin-3-yl-2,3-dihydro-imidazo[4,5-c]quinolin-1-yl)-phenyl]-propionitrile salt;

152-36) 4-Toluenesulfonic acid 2-methyl-2-[4-(3-methyl-2-oxo-5-oxy-8-quinolin-3-yl-2,3-dihydro-imidazo[4,5-c]quinolin-1-yl)-phenyl]-propionitrile salt;

152-37) 4-Toluenesulfonic acid 2-[4-(7-fluoro-3-methyl-2-oxo-8-pyridin-3-yl-2,3-dihydro-imidazo[4,5-c]quinolin-1-yl)-phenyl]-2-methyl-propionitrile salt;

152-38) 4-Toluenesulfonic acid 2-[4-(7-fluoro-3-methyl-2-oxo-8-quinolin-3-yl-2,3-dihydro-imidazo[4,5-c]quinolin-1-yl)-phenyl]-2-methyl-propionitrile salt;

152-39) 4-Toluenesulfonic acid N-Methyl-N-[4-(3-methyl-2-oxo-8-pyridin-3-yl-2,3-dihydro-imidazo[4,5-c]quinolin-1-yl)-phenyl]-methanesulfonamide salt;

152-40) 4-Toluenesulfonic acid ethanesulfonic acid methyl-[4-(3-methyl-2-oxo-8-pyridin-3-yl-2,3-dihydro-imidazo[4,5-c]quinolin-1-yl)-phenyl]-amide salt;

152-41) 4-Toluenesulfonic acid ethanesulfonic acid methyl-[4-(3-methyl-2-oxo-8-quinolin-3-yl-2,3-dihydro-imidazo[4,5-c]quinolin-1-yl)-phenyl]-amide salt;

152-42) 4-Toluenesulfonic acid N-ethyl-N-[4-(3-methyl-2-oxo-8-pyridin-3-yl-2,3-dihydro-imidazo[4,5-c]quinolin-1-yl)-phenyl]-methanesulfonamide salt;

152-43) 4-Toluenesulfonic acid N-ethyl-N-[4-(3-methyl-2-oxo-8-quinolin-3-yl-2,3-dihydro-imidazo[4,5-c]quinolin-1-yl)-phenyl]-methanesulfonamide salt;

152-44) 4-Toluenesulfonic acid 2-[4-(3-ethyl-2-oxo-8-pyridin-3-yl-2,3-dihydro-imidazo[4,5-c]quinolin-1-yl)-phenyl]-2-methyl-propionitrile salt;

152-45) 4-Toluenesulfonic acid 1-[3-fluoro-4-(4-methanesulfonyl-piperazin-1-yl)-phenyl]-3-methyl-8-quinolin-3-yl-1,3-dihydro-imidazo[4,5-c]quinolin-2-one salt;

152-46) 4-Toluenesulfonic acid 1-[3-fluoro-4-(4-methanesulfonyl-piperazin-1-yl)-phenyl]-3-methyl-8-pyridin-3-yl-1,3-dihydro-imidazo[4,5-c]quinolin-2-one salt;

152-47) 4-Toluenesulfonic acid 1-[3-chloro-4-(4-methyl-piperazin-1-yl)-phenyl]-3-methyl-8-quinolin-3-yl-1,3-dihydro-imidazo[4,5-c]quinolin-2-one salt;

152-48) 4-Toluenesulfonic acid 1-[3-chloro-4-(4-methyl-piperazin-1-yl)-phenyl]-3-methyl-8-pyridin-3-yl-1,3-dihydro-imidazo[4,5-c]quinolin-2-one salt;

152-49) 4-Toluenesulfonic acid 1-(4-imidazol-1-yl-2-methyl-phenyl)-3-methyl-8-pyridin-3-yl-1,3-dihydro-imidazo[4,5-c]quinolin-2-one salt;

152-50) 4-Toluenesulfonic acid 3-methyl-1-(4-pyrazol-1-yl-phenyl)-8-pyridin-3-yl-1,3-dihydro-imidazo[4,5-c]quinolin-2-one salt;

152-51) 4-Toluenesulfonic acid 1-(3-chloro-4-imidazol-1-yl-phenyl)-3-methyl-8-pyridin-3-yl-1,3-dihydro-imidazo[4,5-c]quinolin-2-one salt;

152-52) 4-Toluenesulfonic acid 1-(3-chloro-4-imidazol-1-yl-phenyl)-3-methyl-8-quinolin-3-yl-1,3-dihydro-imidazo[4,5-c]quinolin-2-one salt;

152-53) 4-Toluenesulfonic acid 2-methyl-2-[4-(3-methyl-8-quinolin-3-yl-2-thioxo-2,3-dihydro-imidazo[4,5-c]quinolin-1-yl)-phenyl]-propionitrile salt;

152-54) 4-Toluenesulfonic acid 2-methyl-2-{4-[3-methyl-8-(2-methyl-pyridin-4-yl)-2-oxo-2,3-dihydro-imidazo[4,5-c]quinolin-1-yl]-phenyl}-propionitrile salt;

152-55) 4-Toluenesulfonic acid 1-[4-(3-methyl-2-oxo-8-pyridin-3-yl-2,3-dihydro-imidazo[4,5-c]quinolin-1-yl)-phenyl]-cyclopropanecarbonitrile salt;

152-56) 4-Toluenesulfonic acid 1-[4-(3-methyl-2-oxo-8-quinolin-3-yl-2,3-dihydro-imidazo[4,5-c]quinolin-1-yl)-phenyl]-cyclopropanecarbonitrile salt;

152-57) 4-Toluenesulfonic acid 1-{4-[8-(6-methoxy-pyridin-3-yl)-3-methyl-2-oxo-2,3-dihydro-imidazo[4,5-c]quinolin-1-yl]-phenyl}-cyclopropanecarbonitrile salt;

152-58) 4-Toluenesulfonic acid 1-(3-chloro-4-piperazin-1-yl-phenyl)-3-methyl-8-pyrimidin-5-yl-1,3-dihydro-imidazo[4,5-c]quinolin-2-one salt;

152-59) 4-Toluenesulfonic acid 8-(6-methoxy-pyridin-3-yl)-3-methyl-1-(4-[1,2,4]triazol-1-yl-3-trifluoromethyl-phenyl)-1,3-dihydro-imidazo[4,5-c]quinolin-2-one salt;

152-60) 4-Toluenesulfonic acid 1-(3-chloro-4-[1,2,4]triazol-1-yl-phenyl)-3-methyl-8-pyridin-3-yl-1,3-dihydro-imidazo[4,5-c]quinolin-2-one salt;

152-61) 4-Toluenesulfonic acid 1-(3-chloro-4-[1,2,4]triazol-1-yl-phenyl)-3-methyl-8-quinolin-3-yl-1,3-dihydro-imidazo[4,5-c]quinolin-2-one salt;

152-62) 4-Toluenesulfonic acid 1-(4-imidazol-1-yl-3-trifluoromethyl-phenyl)-3-methyl-8-pyridin-3-yl-1,3-dihydro-imidazo[4,5-c]quinolin-2-one salt;

152-63) 4-Toluenesulfonic acid 1-(4-imidazol-1-yl-3-trifluoromethyl-phenyl)-3-methyl-8-quinolin-3-yl-1,3-dihydro-imidazo[4,5-c]quinolin-2-one salt;

152-64) 4-Toluenesulfonic acid 1-(4-imidazol-1-yl-3-trifluoromethyl-phenyl)-8-(6-methoxy-pyridin-3-yl)-3-methyl-1,3-dihydro-imidazo[4,5-c]quinolin-2-one salt;

152-65) 4-Toluenesulfonic acid 3-methyl-8-quinolin-3-yl-1-(4-[1,2,4]triazol-1-ylmethyl-phenyl)-1,3-dihydro-imidazo[4,5-c]quinolin-2-one salt;

152-66) 4-Toluenesulfonic acid 1-(4-imidazol-1-ylmethyl-phenyl)-3-methyl-8-quinolin-3-yl-1,3-dihydro-imidazo[4,5-c]quinolin-2-one salt.

Example 153

The following maleic acid salts are prepared in a stoichiometric ratio of 1:1 following standard reaction conditions in analogy to or according to methods that are known in the art.

153-1) Maleic acid 2-methyl-2-{4-[3-methyl-2-oxo-8-(6-piperazin-1-yl-pyridin-3-yl)-2,3-dihydro-imidazo[4,5-c]quinolin-1-yl]-phenyl}-propionitrile salt;

153-2) Maleic acid 1-(3-fluoro-4-piperazin-1-yl-phenyl)-3-methyl-8-quinolin-3-yl-1,3-dihydro-imidazo[4,5-c]quinolin-2-one salt;

153-3) Maleic acid 1-(3-fluoro-4-piperazin-1-yl-phenyl)-3-methyl-8-pyridin-3-yl-1,3-dihydro-imidazo[4,5-c]quinolin-2-one salt;

153-4) Maleic acid 3-methyl-1-[4-(4-methyl-piperazin-1-yl)-phenyl]-8-quinolin-3-yl-1,3-dihydro-imidazo[4,5-c]quinolin-2-one salt;

153-5) Maleic acid 3-methyl-1-[4-(4-methyl-piperazin-1-yl)-phenyl]-8-pyridin-3-yl-1,3-dihydro-imidazo[4,5-c]quinolin-2-one salt;

153-6) Maleic acid 3-methyl-1-[4-(4-methyl-piperazin-1-yl)-3-trifluoromethyl-phenyl]-8-quinolin-3-yl-1,3-dihydro-imidazo[4,5-c]quinolin-2-one salt;

153-7) Maleic acid 3-methyl-1-[4-(4-methyl-piperazin-1-yl)-3-trifluoromethyl-phenyl]-8-pyridin-3-yl-1,3-dihydro-imidazo[4,5-c]quinolin-2-one salt;

153-8) Maleic acid 1-(3-chloro-4-piperazin-1-yl-phenyl)-3-methyl-8-quinolin-3-yl-1,3-dihydro-imidazo[4,5-c]quinolin-2-one salt;

153-9) Maleic acid 1-(3-chloro-4-piperazin-1-yl-phenyl)-3-methyl-8-pyridin-3-yl-1,3-dihydro-imidazo[4,5-c]quinolin-2-one salt;

153-10) Maleic acid 1-(3-chloro-4-piperazin-1-yl-phenyl)-8-(6-methoxy-pyridin-3-yl)-3-methyl-1,3-dihydro-imidazo[4,5-c]quinolin-2-one salt;

153-11) Maleic acid 1-(3-chloro-4-piperazin-1-yl-phenyl)-8-(5-methoxy-pyridin-3-yl)-3-methyl-1,3-dihydro-imidazo[4,5-c]quinolin-2-one salt;

153-12) Maleic acid 1-(3-chloro-4-piperazin-1-yl-phenyl)-3-methyl-8-quinoxalin-6-yl-1,3-dihydro-imidazo[4,5-c]quinolin-2-one salt;

153-13) Maleic acid 3-methyl-1-(4-piperazin-1-yl-3-trifluoromethyl-phenyl)-8-quinolin-3-yl-1,3-dihydro-imidazo[4,5-c]quinolin-2-one salt;

153-14) Maleic acid 3-methyl-1-(4-piperazin-1-yl-3-trifluoromethyl-phenyl)-8-pyridin-3-yl-1,3-dihydro-imidazo[4,5-c]quinolin-2-one salt;

153-15) Maleic acid 8-(6-methoxy-pyridin-3-yl)-3-methyl-1-(4-piperazin-1-yl-3-trifluoromethyl-phenyl)-1,3-dihydro-imidazo[4,5-c]quinolin-2-one salt;

153-16) Maleic acid 8-(5-methoxy-pyridin-3-yl)-3-methyl-1-(4-piperazin-1-yl-3-trifluoromethyl-phenyl)-1,3-dihydro-imidazo[4,5-c]quinolin-2-one salt;

153-17) Maleic acid 3-methyl-1-(4-piperazin-1-yl-3-trifluoromethyl-phenyl)-8-quinoxalin-6-yl-1,3-dihydro-imidazo[4,5-c]quinolin-2-one salt;

153-18) Maleic acid 1-[3-chloro-4-(4-ethyl-piperazin-1-yl)-phenyl]-3-methyl-8-quinolin-3-yl-1,3-dihydro-imidazo[4,5-c]quinolin-2-one salt;

153-19) Maleic acid 1-[3-chloro-4-(4-isopropyl-piperazin-1-yl)-phenyl]-3-methyl-8-quinolin-3-yl-1,3-dihydro-imidazo[4,5-c]quinolin-2-one salt;

153-20) Maleic acid 1-[4-(cis-3,5-dimethyl-piperazin-1-yl)-3-trifluoromethyl-phenyl]-3-methyl-8-pyridin-3-yl-1,3-dihydro-imidazo[4,5-c]quinolin-2-one salt;

153-21) Maleic acid 1-[4-(cis-3,5-dimethyl-piperazin-1-yl)-3-trifluoromethyl-phenyl]-3-methyl-8-quinolin-3-yl-1,3-dihydro-imidazo[4,5-c]quinolin-2-one salt;

153-22) Maleic acid 1-[4-(4-ethyl-piperazin-1-yl)-3-trifluoromethyl-phenyl]-3-methyl-8-pyridin-3-yl-1,3-dihydro-imidazo[4,5-c]quinolin-2-one salt;

153-23) Maleic acid 3-methyl-8-(6-piperazin-1-yl-pyridin-3-yl)-1-(3-trifluoromethyl-phenyl)-1,3-dihydro-imidazo[4,5-c]quinolin-2-one salt;

153-24) Maleic acid 1-(3-chloro-4-piperazin-1-yl-phenyl)-3-methyl-8-(2-methyl-pyridin-4-yl)-1,3-dihydro-imidazo[4,5-c]quinolin-2-one salt;

153-25) Maleic acid 1-[3-chloro-4-(cis-3,5-dimethyl-piperazin-1-yl)-phenyl]-8-(6-methoxy-pyridin-3-yl)-3-methyl-1,3-dihydro-imidazo[4,5-c]quinolin-2-one salt;

153-26) Maleic acid 1-[3-chloro-4-(cis-3,5-dimethyl-piperazin-1-yl)-phenyl]-8-(5-methoxy-pyridin-3-yl)-3-methyl-1,3-dihydro-imidazo[4,5-c]quinolin-2-one salt;

153-27) Maleic acid 1-[4-(cis-3,5-dimethyl-piperazin-1-yl)-3-trifluoromethyl-phenyl]-8-(6-methoxy-pyridin-3-yl)-3-methyl-1,3-dihydro-imidazo[4,5-c]quinolin-2-one salt;

153-28) Maleic acid 1-[4-(cis-3,5-dimethyl-piperazin-1-yl)-3-trifluoromethyl-phenyl]-8-(5-methoxy-pyridin-3-yl)-3-methyl-1,3-dihydro-imidazo[4,5-c]quinolin-2-one salt;

153-29) Maleic acid 8-(2-methoxy-pyrimidin-5-yl)-3-methyl-1-(4-piperazin-1-yl-3-trifluoromethyl-phenyl)-1,3-dihydro-imidazo[4,5-c]quinolin-2-one salt;

153-30) Maleic acid 3-methyl-1-(4-piperazin-1-yl-3-trifluoromethyl-phenyl)-8-pyrimidin-5-yl-1,3-dihydro-imidazo[4,5-c]quinolin-2-one salt;

153-31) Maleic acid 3-methyl-8-(2-methyl-pyridin-4-yl)-1-(4-piperazin-1-yl-3-trifluoromethyl-phenyl)-1,3-dihydro-imidazo[4,5-c]quinolin-2-one salt;

153-32) Maleic acid 8-(3,4-dimethoxy-phenyl)-3-methyl-1-(4-piperazin-1-yl-3-trifluoromethyl-phenyl)-1,3-dihydro-imidazo[4,5-c]quinolin-2-one salt.

Example 154

Soft Capsules 5000 soft gelatin capsules, each comprising as active ingredient 0.05 g of one of the compounds of formula I mentioned in the preceding Examples, are prepared as follows:

Composition

Active Ingredient 250 g

Lauroglycol 2 litres

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:

1. 2-Methyl-2-[4-(3-methyl-2-oxo-8-quinolin-3-yl,2,3-dihydro-imidazo[4,5-c]quinolin-1-yl)-phenyl]-propionitrile.

2. 4-Toluenesulfonic acid 2-methyl-2-[4-(3-methyl-2-oxo-8-quinolin-3-yl,2,3-dihydro-imidazo[4,5-c]quinolin-1-yl)-phenyl]-propionitrile salt.

* * * * *